(12) United States Patent
Tawiah

(10) Patent No.: US 11,717,737 B2
(45) Date of Patent: *Aug. 8, 2023

(54) ATHLETIC TRAINING SYSTEM AND METHOD

(71) Applicant: NIKE, Inc., Beaverton, OR (US)

(72) Inventor: Daniel Tawiah, Amsterdam (NL)

(73) Assignee: NIKE, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/493,515

(22) Filed: Oct. 4, 2021

(65) Prior Publication Data

US 2022/0062735 A1    Mar. 3, 2022

Related U.S. Application Data

(63) Continuation of application No. 16/799,186, filed on Feb. 24, 2020, now Pat. No. 11,161,026, which is a (Continued)

(51) Int. Cl.
*A63B 71/06* (2006.01)
*G16H 20/30* (2018.01)
(Continued)

(52) U.S. Cl.
CPC ...... *A63B 71/0605* (2013.01); *A63B 24/0006* (2013.01); *A63B 24/0021* (2013.01); *A63B 24/0084* (2013.01); *A63B 24/0087* (2013.01); *A63B 71/03* (2020.08); *A63F 13/00* (2013.01); *A63F 13/65* (2014.09); *G06V 20/42* (2022.01); *G16H 20/30* (2018.01); *H04N 7/181* (2013.01); *A63B 24/0075* (2013.01); *A63B 43/00* (2013.01); *A63B 71/02* (2013.01); (Continued)

(58) Field of Classification Search
CPC .......................... G06K 9/0072; A63B 24/0087
See application file for complete search history.

(56) References Cited

U.S. PATENT DOCUMENTS 5,363,297 A    11/1994    Larson et al.
5,745,126 A    4/1998    Jain et al.
(Continued)

FOREIGN PATENT DOCUMENTS

EP    773514 A1    5/1997
GB    2357207 A    6/2001
(Continued)

OTHER PUBLICATIONS

Mar. 11, 2014—(EP) ESR—App. No. 13194071.0.
(Continued)

*Primary Examiner* — Jerry T Jean Baptiste
(74) *Attorney, Agent, or Firm* — Banner & Witcoff, Ltd.

(57) ABSTRACT

An athletic training system (200) has a data recording system (202) and a data engine (204). The data recording system (202) is configured to record an athletic competition event. The event may have a first team of players competing against a second team of players. The data engine (204) is configured to receive data associated with the recorded athletic competition event. The data engine (204) processes the data and displays the data as a replay of the event in animated form.

19 Claims, 25 Drawing Sheets

Related U.S. Application Data continuation of application No. 15/695,374, filed on Sep. 5, 2017, now Pat. No. 10,603,570, which is a continuation of application No. 12/324,638, filed on Nov. 26, 2008, now Pat. No. 9,782,660.

(60) Provisional application No. 60/991,609, filed on Nov. 30, 2007.

(51) Int. Cl.

| | |
|---|---|
| *A63B 24/00* | (2006.01) |
| *H04N 7/18* | (2006.01) |
| *A63F 13/00* | (2014.01) |
| *A63F 13/65* | (2014.01) |
| *G06V 20/40* | (2022.01) |
| *A63B 71/02* | (2006.01) |
| *A63B 43/00* | (2006.01) |
| *A63B 102/24* | (2015.01) |
| *A63B 102/32* | (2015.01) |
| *A63B 102/22* | (2015.01) |
| *A63B 102/18* | (2015.01) |

(52) U.S. Cl.
CPC .......... *A63B 2024/0009* (2013.01); *A63B 2024/0025* (2013.01); *A63B 2024/0096* (2013.01); *A63B 2071/0647* (2013.01); *A63B 2102/18* (2015.10); *A63B 2102/22* (2015.10); *A63B 2102/24* (2015.10); *A63B 2102/32* (2015.10); *A63B 2220/13* (2013.01); *A63B 2220/30* (2013.01); *A63B 2220/40* (2013.01); *A63B 2220/803* (2013.01); *A63B 2220/806* (2013.01); *A63B 2220/836* (2013.01); *A63B 2225/20* (2013.01); *A63B 2225/50* (2013.01); *A63B 2230/06* (2013.01); *A63B 2230/207* (2013.01); *A63B 2243/0025* (2013.01); *A63B 2243/0037* (2013.01); *A63B 2243/0066* (2013.01); *A63F 2300/69* (2013.01); *A63F 2300/8011* (2013.01)

(56) References Cited

U.S. PATENT DOCUMENTS

| | | | |
|---|---|---|---|
| 6,124,862 A | 9/2000 | Boyken et al. | |
| 6,227,974 B1 | 5/2001 | Eilat et al. | |
| 6,441,846 B1 | 8/2002 | Carlbom et al. | |
| 6,710,713 B1 * | 3/2004 | Russo | A63B 24/0021 348/157 |
| 7,216,092 B1 | 5/2007 | Weber et al. | |
| 7,620,466 B2 | 11/2009 | Neale et al. | |
| 7,854,669 B2 | 12/2010 | Marty et al. | |
| 7,868,914 B2 | 1/2011 | Dengler et al. | |
| 7,899,307 B1 | 3/2011 | Hughes | |
| 2001/0005600 A1 | 6/2001 | Ohuchi et al. | |
| 2001/0044758 A1 | 11/2001 | Talib et al. | |
| 2002/0132211 A1 | 9/2002 | August et al. | |
| 2002/0173365 A1 * | 11/2002 | Boscha | A63B 69/362 473/131 |
| 2003/0030734 A1 | 2/2003 | Gibbs et al. | |
| 2003/0142210 A1 | 7/2003 | Carlbom et al. | |
| 2003/0236140 A1 | 12/2003 | Alford | |
| 2004/0194129 A1 * | 9/2004 | Carlbom | H04N 21/8133 348/E7.086 |
| 2006/0294564 A1 | 12/2006 | Guillorit | |
| 2007/0279494 A1 | 12/2007 | Aman et al. | |
| 2008/0161113 A1 * | 7/2008 | Hansen | A63F 13/335 463/42 |
| 2008/0188353 A1 | 8/2008 | Vitolo et al. | |
| 2008/0192116 A1 | 8/2008 | Tamir et al. | |
| 2008/0312010 A1 | 12/2008 | Marty et al. | |
| 2009/0290848 A1 | 11/2009 | Brown | |
| 2010/0137045 A2 | 6/2010 | Angelopoulos | |

FOREIGN PATENT DOCUMENTS

| | | |
|---|---|---|
| JP | H07162744 A | 6/1995 |
| JP | H09220308 A | 8/1997 |
| JP | H10314357 A | 12/1998 |
| JP | H11339009 A | 12/1999 |
| JP | 2001273500 A | 10/2001 |
| JP | 2002365018 A | 12/2002 |
| JP | 2003033461 A | 2/2003 |
| JP | 2004016738 A | 1/2004 |
| JP | 2005211666 A | 8/2005 |
| JP | 2006130127 A | 5/2006 |
| WO | 9846029 A1 | 10/1998 |
| WO | 0044449 A1 | 8/2000 |
| WO | 2005099423 A2 | 10/2005 |
| WO | 2006065679 A2 | 6/2006 |
| WO | 2006103662 A2 | 10/2006 |
| WO | 2016003320 A1 | 1/2016 |

OTHER PUBLICATIONS

Mar. 20, 2009—(WO) Partial ISR—App. No. PCT/US08/085143.
Jun. 10, 2010—(WO) IPRP—App. No. PCT/US08/085143.
Jul. 7, 2009—(WO) ISR & WO—App. No. PCT/US08/085143.

* cited by examiner

ATHLETIC TRAINING SYSTEM AND METHOD

RELATED APPLICATIONS

This application is a continuation of U.S. patent application Ser. No. 16/799,186 filed Feb. 24, 2020, which is a continuation of and claims priority to U.S. patent application Ser. No. 15/695,374 filed Sep. 5, 2017, which is a continuation of and claims priority to U.S. patent application Ser. No. 12/324,638 filed Nov. 26, 2008 which claims the benefit of U.S. Patent Application No. 60/991,609 filed on Nov. 30, 2007, which applications are incorporated by reference herein and made a part hereof.

FIELD OF THE INVENTION

Aspects of the present disclosure are generally directed to an athletic training system and method. More specifically, aspects of the disclosure provide a data recording system and a data or display engine that utilizes data recorded from a sporting event and uniquely displays the data for utilization in athletic training.

BACKGROUND

Athletic competition and physical fitness has become increasingly popular over time. Participants are constantly seeking new ways to improve athletic performance or fitness levels. Technological advancements have allowed participants to better monitor personal performance. Nevertheless, participants are still limited in obtaining accurate personal performance data such as when competing in a sporting event. For example, while certain end results can be easily quantified such as goals or points scored, other performance related data is much more difficult to quantify where it can be used for athletic training.

While certain athletic training systems and athletic performance monitoring systems are known and provide a number of advantageous features, they nevertheless have certain limitations. The present invention seeks to overcome certain of these limitations and other drawbacks of the prior art, and to provide new features not heretofore available.

BRIEF SUMMARY OF THE INVENTION

The present invention provides an athletic training system and method.

According to a first aspect of the invention, the athletic training system has a data recording system configured to record an athletic competition event. In one embodiment, the event may have a first team of players competing against a second team of players. The system also has a data engine that in one form is a video game engine configured to receive data associated with the recorded athletic competition event. The engine processes the data and displays the data as a replay of the event in animated form. The data engine may incorporate avatars associated with the players in the event.

According to another aspect of the invention, a method of displaying a sporting event includes the steps of: recording data associated with the sporting event; inputting the data into a video game engine; and processing the data through the video game engine wherein the sporting event is replayed by the video game engine.

BRIEF DESCRIPTION OF THE DRAWINGS

A more complete understanding of the present invention and certain advantages thereof may be acquired by referring to the following description along with the accompanying drawings, in which like reference numbers indicate like features, and wherein:

FIG. 13 illustrates an information interface showing comparisons between two teams according to one or more aspects of the invention described herein;

FIGS. 25 and 26 illustrate additional information interfaces showing different graphical representations according to one or more aspects of the present invention.

DETAILED DESCRIPTION

Figure 1:
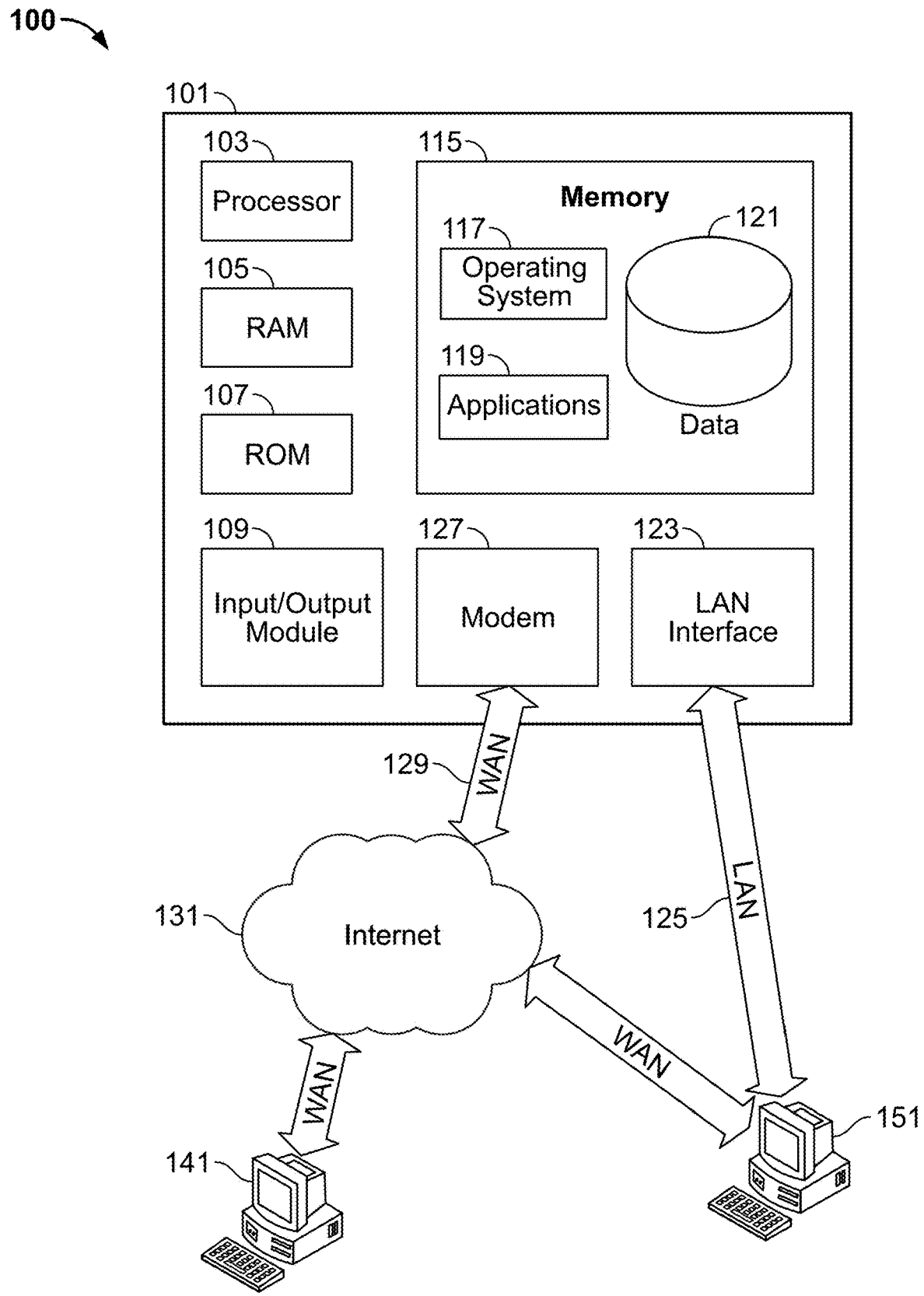
FIG. 1 is a schematic view of a computing system that can be used with the athletic training system of the present invention.

In the following description of various example embodiments of the invention, reference is made to the accompanying drawings, which form a part hereof, and in which are shown by way of illustration various example devices, systems, and environments in which aspects of the invention may be practiced. Other specific arrangements of parts, example devices, systems, and environments may be utilized and structural and functional modifications may be made without departing from the scope of the present invention.

I. General Description of the Athletic Training System and Method According to Aspects of the Invention In general, as described above, aspects of the invention relate to an athletic training system and method. In accordance with at least some aspects, the system provides an athlete, coach, and fan with the ability to record, review, and analyze real athletic events for training and entertainment purposes. Further, the recording and analysis of the real athletic event may provide input to a video game engine such that the video game may better represent real athletes and athletic teams. A video game player may also be able to insert a virtual player under their control into a video game representing, at least in part, a real athletic event in which real athletes participated. The video game player may additionally have one of the real athletes in the real athletic event and the available skills and abilities of their respective virtual player may reflect their real performance.

II. Specific Examples of the Invention

The present invention provides an athletic training system and method, the system generally designated with the reference numeral 200. In some aspects of the invention, users can obtain access to certain portions of the system 200 remotely such as using a computing system environment as described below. Applicants provide a general disclosure of an exemplary computing system environment that can be used with the system 200 followed by a more detailed description of specific components of the system 200.

FIG. 1 illustrates an example of a computing system environment 100 that may be used according to one or more embodiments of the invention. The computing system environment 100 is only one example of a suitable computing environment and is not intended to suggest any limitation as to the scope of use or functionality of the invention. The computing system environment 100 should not be interpreted as having any dependency or requirement relating to any one or combination of the illustrated components.

The invention is operational with numerous other general purpose or special purpose computing system environments or configurations. Examples of well known computing systems, environments, and/or configurations that may be suitable for use with the invention include, but are not limited to, personal computers, server computers, hand-held or laptop devices, multiprocessor systems, microprocessor-based systems, set top boxes, programmable consumer electronics, smart phones, network PCs, minicomputers, mainframe computers, distributed computing environments that include any of the above systems or devices, and the like.

The invention may be described in the general context of computer-executable instructions, such as program modules, being executed by a computer. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

With reference to FIG. 1, the computing system environment 100 may include a computer 101 having a processor 103 for controlling overall operation of the computer 101 and its associated components, including RAM 105, ROM 107, an input/output module or BIOS 109, and a memory 115. The computer 101 typically includes a variety of computer readable media. The computer readable media may be any available media that may be accessed by the computer 101 and may include both volatile and nonvolatile media and removable and non-removable media. By way of example, and not limitation, computer readable media may comprise computer storage media and communication media.

Computer storage media may include volatile and non-volatile and removable and non-removable media implemented in any method or technology for storage of information such as computer readable instructions, data structures, program modules, or other data. Computer storage media includes, but is not limited to, random access memory (RAM), read only memory (ROM), electronically erasable programmable read only memory (EEPROM), flash memory or other memory technology, CD-ROM, digital versatile disks (DVD) or other optical disk storage, magnetic cassettes, magnetic tape, magnetic disk storage or other magnetic storage devices, and any other medium that can be used to store the desired information and that can be accessed by the computer 101.

Communication media may embody computer readable instructions, data structures, program modules, and/or other data in a modulated data signal such as a carrier wave or other transport mechanism. It may also include any information delivery media. Modulated data signal is a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media. Although not shown, RAM 105 may include one or more applications representing the application data stored in RAM 105 while the computer is on and corresponding software applications (e.g., software tasks) are being executed.

The input/output module or BIOS 109 may include a microphone, keypad, touch screen, and/or stylus through which a user of the computer 101 may provide input. The input/output module or BIOS 109 may also include one or more of a speaker for providing audio output and a video display device for providing textual, audiovisual, and/or graphical output.

Software may be stored within memory 115 and/or storage to provide instructions to the processor 103 for enabling the computer 101 to perform various functions. For example, the memory 115 may store software used by the computer 101, such as an operating system 117 and an associated data file 121. Alternatively, some or all of the computer executable instructions for the computer 101 may be embodied in hardware or firmware (not shown). As described in detail below, the data file 121 may provide centralized storage of the organization of the sporting events and/or selection of a player for a team sport.

The computer 101 may operate in a networked environment that supports connections to one or more remote computers, such as computing devices 141 and 151. The computing devices 141 and 151 may be personal computers or servers that include many or all of the elements described above relative to the computer 101. The network connections depicted in FIG. 1 may include a local area network (LAN) 125 and a wide area network (WAN) 129 and may also include other networks. The computer 101 is connected to the LAN 125 through a network interface or adapter 123. The computer 101 may be a server and may include a modem 127 or other means for establishing communications over the WAN 129. For example, the computer 101 may connect to a WAN 129 such as the Internet 131 through a modem connection. The network connections may include any communications link between computers.

The existence of any of various well-known protocols such as TCP/IP, Ethernet, FTP, HTTP and the like is presumed, and the system can be operated in a client-server configuration to permit a user to retrieve web pages from a web-based server. Any of various conventional web browsers can be used to display and manipulate data on web pages.

Additionally, an application program may be used by the computer 101 according to an embodiment of the invention. The application program may include computer executable instructions for invoking user functionality related to communication, such as email, short message service (SMS), and voice input and speech recognition applications.

The computing devices 141 or 151 may also be mobile terminals including various other components, such as a battery, speaker, and antennas (not shown). The input/output module or BIOS 109 may include a user interface including such physical components as a voice interface, one or more arrow keys, joystick, data glove, mouse, roller ball, touch screen, keypads or the like.

Each of the plurality of computing devices 141, 151 may contain software for creating a data file 121. The software may be a set of detailed computer-executable instructions for the computing devices 141, 151. The software may provide the computing devices 141, 151 with the ability to create a data file 121. The data file 121 may contain multiple individual files of information that may each correspond to an individual document.

For example, a plurality of players may each have a player profile and each player profile may be separately contained within the data file 121. Similarly, information about a plurality of sporting events and a plurality of teams may be separately contained within a data file 121 and may be separately contained from the player profile information. Additionally, a report may be generated that includes information relating to one or more sporting events, players, and/or teams in the data file 121.

The computer 101 may include memory 115 for storing computer-readable instructions and a processor 103 for executing the computer-executable instructions. The computer-executable instructions may be data in the form of program source code that may be capable of modifying the data file 121. The computer-executable instructions may be a series or sequence of instructions for a computing device that is typically in the form of a programming language such as C++, Java, SQL, or the like. Various computer programming languages may be used to create the computer-executable instructions, and the invention is not limited to the programming languages listed above.

The memory 115 may be a portion of the computer 101 that stores data or other instructions. The memory 115 may be retained or lost when power is lost to the system. The memory 115 may provide access to data for a user or computing device 141, 151 to revise and manage a data file 121.

The processor 103 may be capable of executing the computer-executable instructions. The computer-executable instructions may be executed by the processor 103 after they have been stored in the memory 115. The processor 103 may be a centralized element within a computing system that is capable of performing computations. For example, the processor 103 may perform the computations that are described in the computer-executable instructions and then execute the computer-executable instructions. The computer-executable instructions may include data describing changes to the data file 121 that were made by a user or computing device 141, 151 over a computer network such as the Internet 131. The server 101 stores the data in the data file 121 that may be associated with a player or team. The data file 121 may be stored in the memory 115 so that it may be accessible to a plurality of computing devices 141, 151 and/or users.

The data that is stored in the data file 121 may include information relating to athletic training. Security precautions may be implemented to prevent unauthorized access to the data file 121. A username and a password may be required to access the data file 121. Some of the data that is stored in the data file 121 may be shared between multiple players, teams, organizers of team sporting events, and the like. Any desirable security precautions may be implemented.

The computer-executable instructions may be a series or sequence of instructions for a computing device 141, 151, described in detail throughout this disclosure. The processor 103 may be configured to execute the computer-executable instructions that may be used to organize a team sporting event. Such computer-executable instructions may be located (e.g., physically or logically) in modules in the memory 115. The computer network 131 may be any network that interconnects users and/or computing devices 141, 151. According to at least one aspect of the invention, the computer network 131 may provide shared access by two computing devices to at least a portion of the data in the plurality of modules. Shared access may be two or more computing devices 141, 151 that may be coupled to the computer network 131 and/or that may be able to communicate with each other and/or access, change, and add data to a data file 121.

A computer network such as the Internet 131 provides access to the date file 121 that may be shared between the computing devices 141, 151. Additionally, the computer network may be public or private and may be wired or wireless. The computing devices 141, 151 that are coupled to the computer network may be any electronic device that is capable of connecting to a computer network and transmitting data over the computer network. Further, the computing devices 141,151 are capable of receiving data for entry into a data file 121 that may be associated with organizing a team sporting event.

Figure 2:
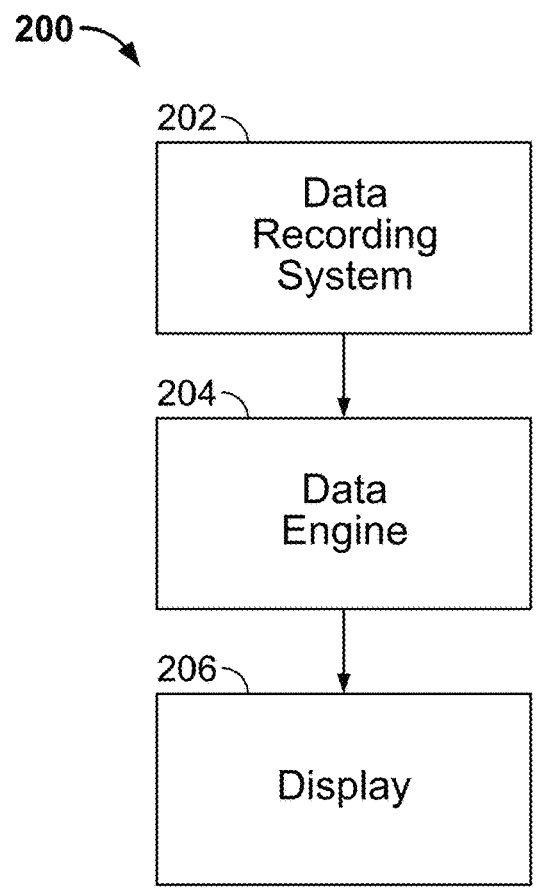
FIG. 2 is a schematic flow diagram of the athletic training system of the present invention.

Referring to FIG. 2, the athletic training system 200 generally includes a data recording system 202 and a data engine 204 or display engine 204. As explained in greater detail below, data associated with a game or athletic competition event is recorded by the data recording system 202. The recorded data is inputted into the data engine 204 and processed wherein the data engine 204 replays the game in a unique form. The data engine 204 has a display 206 operably associated therewith. In certain embodiments, the display 206 may be considered a part of the data engine 204 or display engine 204. The data recording system 202 will first be described followed by a description of the data engine 204 as well as the operable cooperation between these components.

Data Recording System

Figure 3:
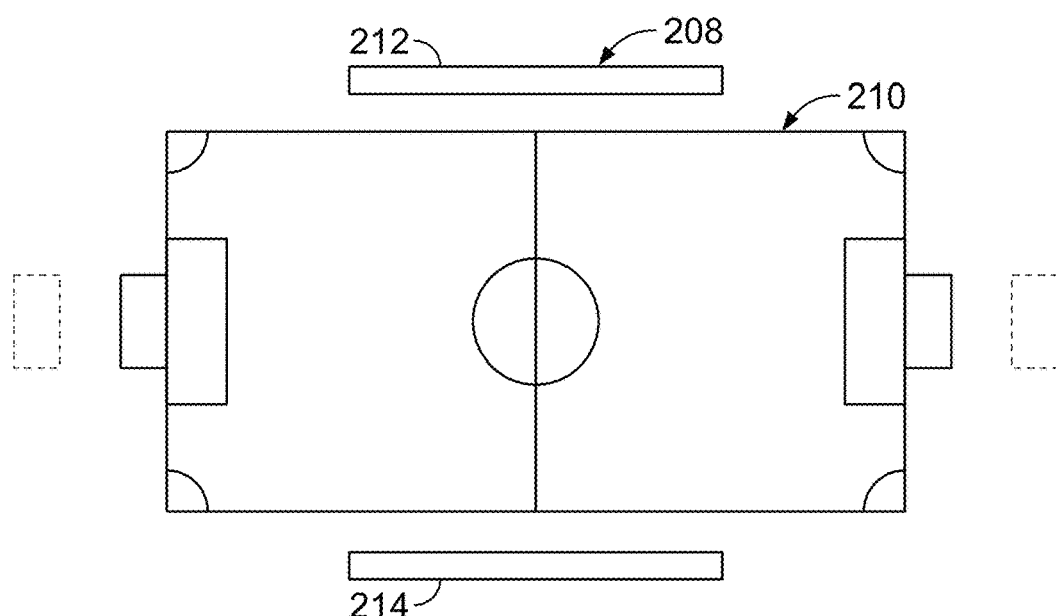
FIG. 3 is a schematic plan view of a pitch or field equipped with a data recording system of the athletic training system of the present invention.

In general, the data recording system 202 includes a plurality of cameras 208 that may jointly identify the position, in real-time, of all moving objects in a sports arena or on a sports pitch or field 210. FIG. 3 shows a schematic view of a football pitch or American soccer field 210. It is understood that the system 200 can be used with various other types of athletic fields. More specifically, in an embodiment sports arena, pitch, or field 210 area may be covered by multiple computer-controlled cameras (e.g., camera assemblies 212 and 214) that interoperate and utilize stereoscopy or similar measurement techniques to capture, process, and deliver the three-dimensional coordinates (e.g., (x,y,z)), speed, and acceleration of each moving object in the sports arena, pitch, or field 210 in the form of a data feed to the data engine 204. The precision of the three-dimensional coordinate measurement for each moving object may meet or exceed one inch. The data recording system 202 of an embodiment may further deliver coordinates in substantially real-time (i.e., $\frac{1}{25}$ second intervals or faster) to the data engine 204. In this manner, the activities of the athletes within the sports arena, pitch, or field 210 may be measured without requiring additional sensors and/or transmitters on the athletes or their equipment. However, in an embodiment and as will be discussed below, the addition of sensors and/or transmitters on the athletes and their equipment may further contribute to the data available for recording, presentation, and analysis.

Referring to FIGS. 3-6, the arena, pitch, or field 210 may have a plurality of cameras set up that will capture and record the game action in real-time. In doing so, the cameras of the data recording system 202 generally will track each individual player or athlete's position and movement (e.g., direction, speed, acceleration and/or any other measurement of the athlete's athletic performance). The cameras will further capture and record the ball position and movement. As noted, the position and movement for both the player or athlete and the ball may be determined and stored in three dimensions so that, for example, the height of a jump and/or the trajectory of a kick, throw, hit or other event may be more realistically captured by the data recording system 202. In an exemplary embodiment, a camera is dedicated to following the movements of a particular player.

In an embodiment, four to eight computer-controlled pairs of cameras interoperate stereoscopically to determine the position and movement of one or more players or athletes and the ball within the sports arena, pitch, or field 210. In an alternate embodiment, two clusters of sixteen computer-controlled cameras determine the position and movement of one or more players or athletes and the ball within the sports arena, pitch, or field 210. It is to be understood that other combinations and configurations of cameras may yield similar determinations of position and movement of both the players and the ball.

For example, and as illustrated by FIGS. 3-6 the cameras may be located substantially surrounding a sports arena, pitch, or field 210. In an embodiment, the cameras may be located approximately ten to fifteen meters above the sports arena, pitch, or field 210. The cameras may be mounted on dedicated stands or they may be mounted or otherwise engaged with the sports arena, stands surrounding the pitch or field, or any other structure associated with the sports arena, pitch, or field 210. For example, for a simple soccer field or other non-permanent athletic venue, the cameras may be mounted on transportable dedicated stands or mounts. The same may be true for a golf course or auto racing course. For more permanent structures such as for basketball, football, baseball, hockey, and similar athletic arenas, the cameras may be mounted on the structure of the stadium or arena. The cameras may be distributed along the entire perimeter of the arena, pitch, or field 210 or may be arranged on individual sides of the arena, pitch, or field 210. The cameras may be set up such that a respective camera focuses on the movement of a respective player or the ball for the entire duration of the game or competition.

Once a data recording system 202 has been installed and calibrated, the data recording system may capture and record the events occurring in the arena, pitch, or field 210. While substantially or completely automated, a trained operator may nevertheless oversee the operation of the data recording system 202 during the event. As shown in an embodiment in FIG. 3, the data recording system 202 may have a first camera assembly 212 having a plurality of cameras positioned along one side of the sports arena, pitch, or field 210. The data recording system 202 may also have a second camera assembly 214 having a plurality of cameras positioned along an opposite side of the sports arena, pitch, or field 210. It is understood that more or fewer camera assemblies can be used such as shown in phantom lines in FIG. 3. Each camera assemblies can use a varying number of cameras as desired. As discussed, the number and position of the camera assemblies can vary as desired consistent with the size of the sports arena, pitch, or field 210, the complexity of the activities within the arena, pitch, or field 210, and/or the number of players or athletes participating in the game, competition, or the like. FIG. 3 further shows in phantom that additional camera assemblies may be positioned at ends of the pitch 210 or field 210.

Figure 4:
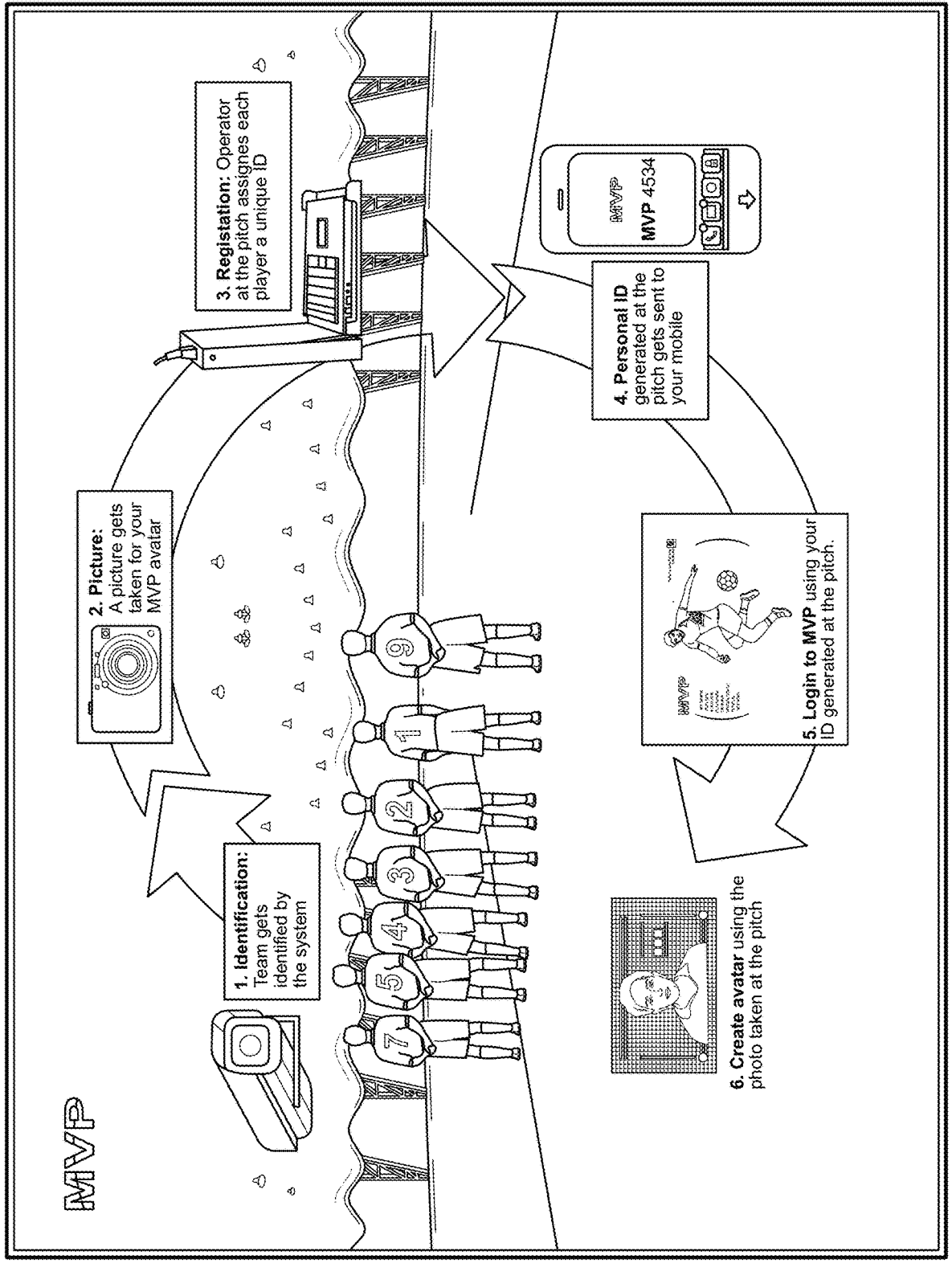
FIG. 4 is a schematic view of a setup process according to one or more aspects of the invention described herein.

As illustrated by FIG. 4, before the event begins, for example during the athletes' pre-game warm up, the trained operator may facilitate the capture and identification of the athletes involved in the event. In an embodiment, the trained operator and/or data recording system 202 may assign a unique identifier to each athlete. The unique identifier may relate to the athletes cell phone number, jersey number, or any other manner by which the athletes may be uniquely identified. Further, in an embodiment, each athlete may wear a transducer, transmitter, or transceiver containing identification data that may interface with the data recording system 202. For example, in an embodiment each athlete may wear a radio frequency identification tag (RFID tag) that contains identification data that may be read by the data recording system 202 to identify the athlete. For either embodiment, the data recording system 202 may include face or shape recognition processing to aid identifying and following athletes once the game or competition has begun. Additionally or alternatively, the face or shape recognition processing may facilitate the creation of one or more avatars that may represent the athletes during the replay of the event, game, or competition and/or as part of a video game as will be described below in more detail.

Figure 5:
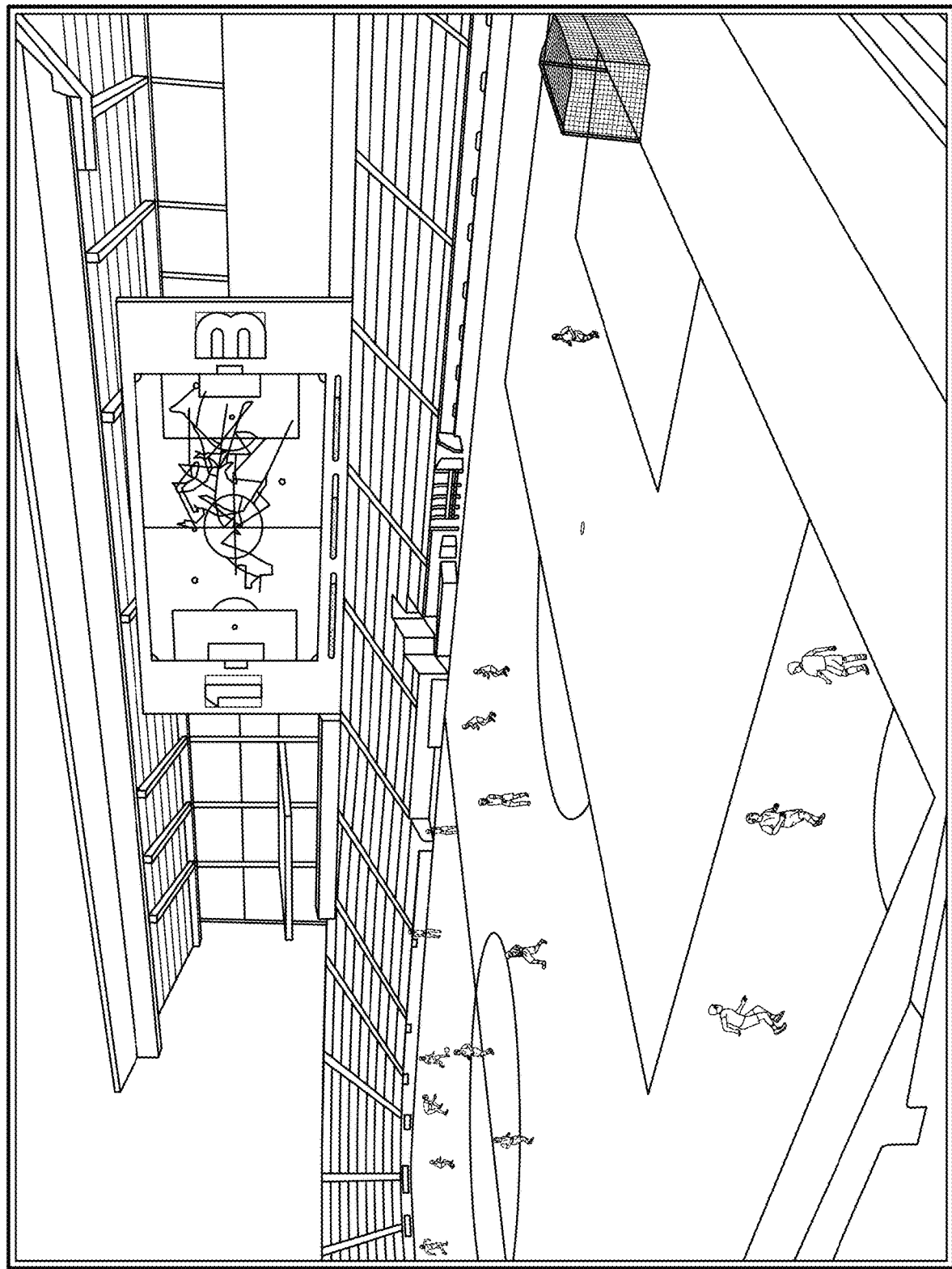
FIG. 5 is a schematic view of a pitch or field that can be utilized with the system of the present invention.
Figure 6:
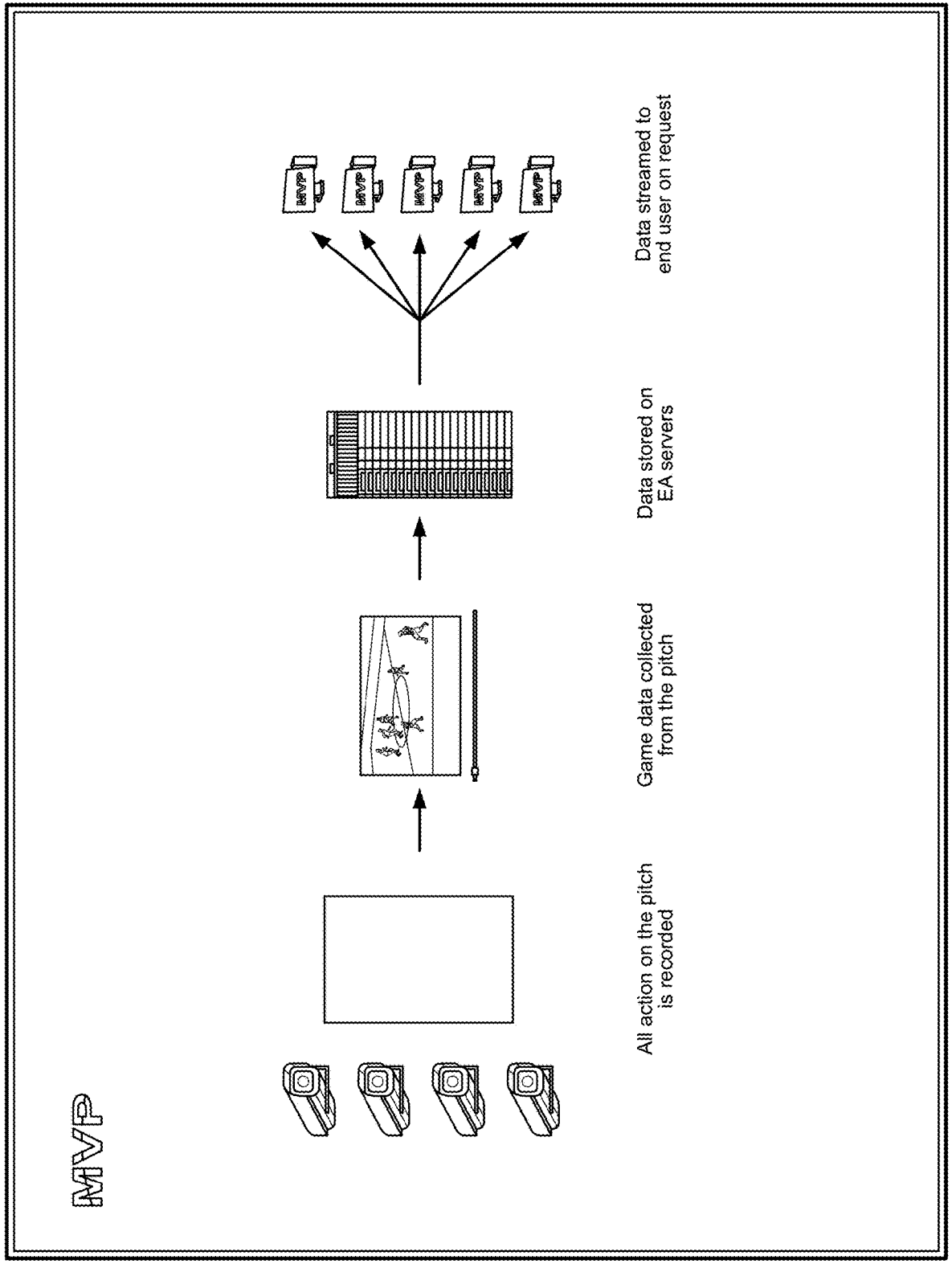
FIG. 6 is a schematic view showing a flow path of an exemplary embodiment of the present invention.

FIGS. 5 and 6 illustrate that during the event, game, or competition, the data recording system 202 may record the position of each athlete and the ball or puck. The movement of each may be calculated as the rate of change of the position of each as determined by the data recording system 202. Once the data recording system 202 captures and computes the position and movement of each athlete and the ball or puck, the resulting position and movement data may be stored for later analysis or streamed in real time to end users. For each embodiment, the position and movement data may be analyzed to thereafter or in real-time reproduce the event, game, or competition. For example, the bandwidth required to stream position and movement data for reconstruction into a virtual event, game, or competition, for example by a computer user who is watching the event, game, or competition in real-time over the Internet, may be substantially less than the bandwidth required to stream the live video feed itself.

Data/Display/Engine

Once the event, competition, or game has been recorded at least in the form of the position and movement of one or more athletes and the ball, puck, or other athletic device, the event, competition, or game may be analyzed, reviewed, and/or otherwise recalled. More specifically, the data engine 204 or display engine 204 may receive and interpret the data provided by the data recording system. In general, the data engine 204 and/or display engine 206 may allow the event, competition, or game to be viewed from multiple angles. The data engine 204 and/or display engine 206 may also provide coaching tools based on the athletic performance of an athlete or a team. The data engine 204 and/or display engine 206 may further generate, alter, and/or enhance a sports video game. Each embodiment will be discussed in turn, though in an embodiment the data engine 204 or display engine 204 may perform multiple or all of the functions introduced above. Thus, the recorded data from the recording system 202 is transferred to the display engine 204 wherein the display engine 204 can replay the data, such as in animated form, and display such data as shown in the following figures.

Figure 7:
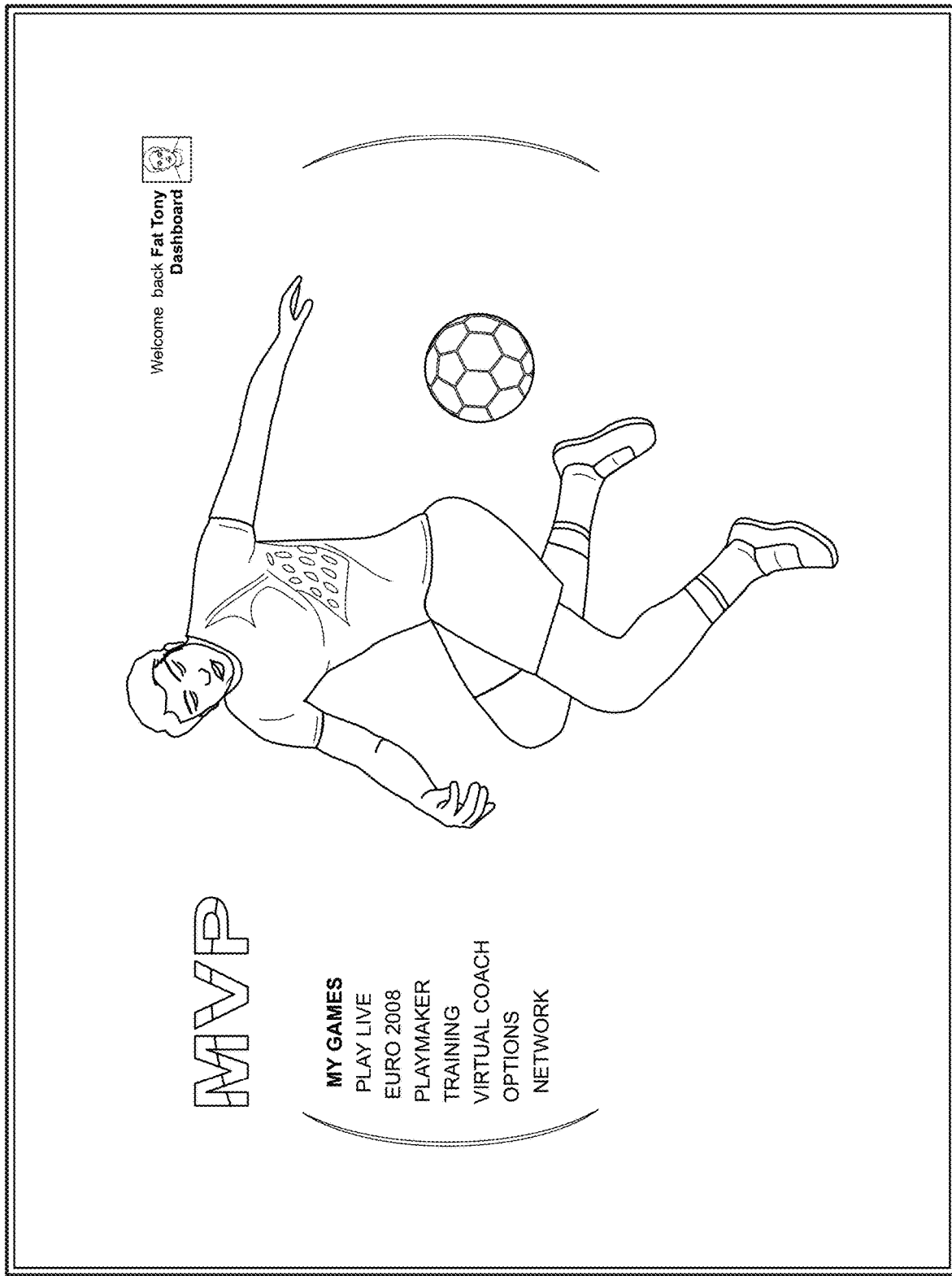
FIGS. 7 and 8 illustrate interfaces according to one or more aspects of the invention described herein.

FIG. 7 illustrates that once the data recording system 202 has captured and recorded the event, game, or competition (i.e., the position and movement of each player and the ball, puck, or other athletic device), it may thereafter be analyzed in a variety of fashions. For example, the data recording system 202 of an embodiment may allow an athlete to analyze individual events, games, or competitions in which they have participate, including watching virtual replays of the events, games, or competitions. For example, the data recording system 202 may calculate the total distance run by each athlete, the average and top speeds of each athlete, the endurance of the athlete (e.g., as measured by at least a combination of total distance run and average speed), the throwing, passing, kicking, and/or hitting accuracy of the athlete, and the like depending on the specific event, game, or competition.

Figure 9:
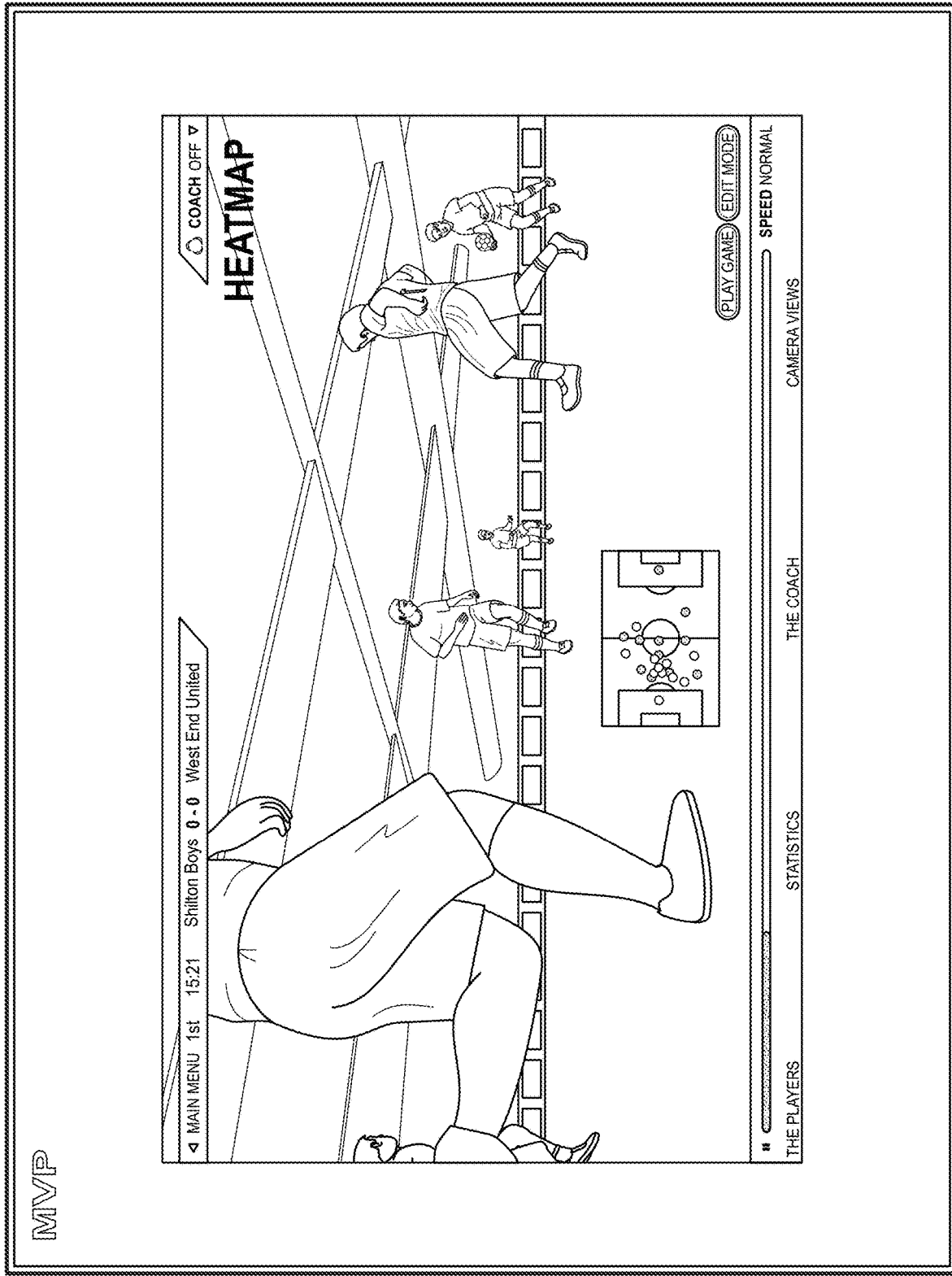
FIG. 9 illustrates a frequency mapping interface according to one or more aspects of the invention described herein.

Further, as illustrated by FIG. 9, the data recording system 202 may generate a map of the frequency with which each athlete occupies particular portions of the arena, pitch, or field. For example, such a "heat map" may be useful to determine if an athlete occupies the position of the arena, pitch, or field commensurate with their position and the like. Plus, the heat map may be correlated with, for example, endurance and the throwing, passing, kicking, and/or hitting accuracy to determine if the player spends too much time running around with or without the ball, puck, or other athletic device and whether they are more successful in throwing, passing, or hitting in certain parts of the arena, pitch, or field.

Figure 8:
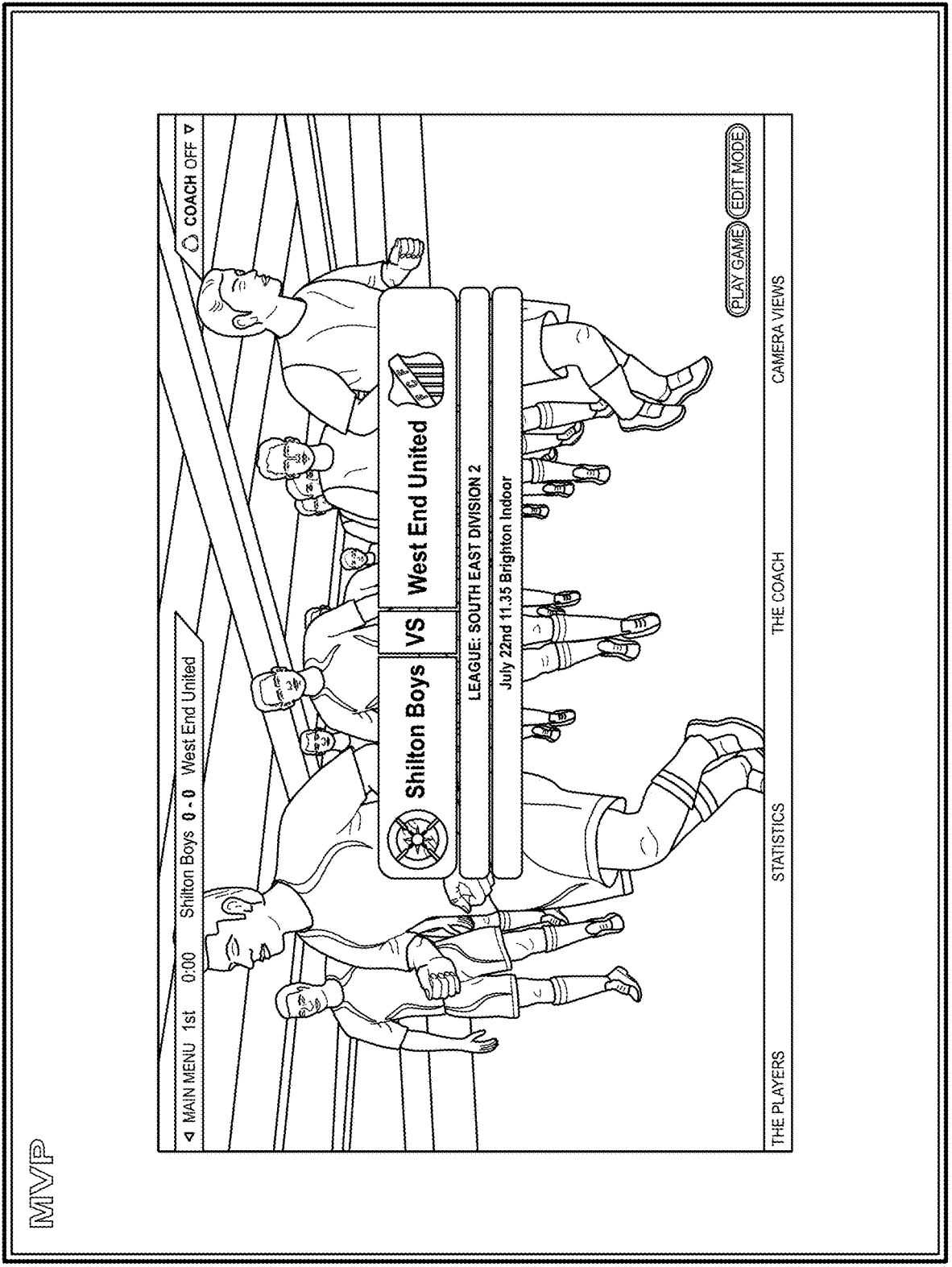

FIG. 8 illustrates that once the data recording system 202 has captured and recorded data related to the position and movement of players and athletes, the data engine 204 may utilize the data to reconstruct the event, competition, or game at a later time or in real time. For example, streaming data (e.g., over the Internet) may be thereafter reconstructed by the display engine 204 on a viewer's computer, such as through a typical computing system described above, so that the viewer may watch the event, competition, or game substantially in real time without demanding the bandwidth that would be required by streaming the video capture or recording. Further, the display engine 204 may allow alternate points of view or angles. For example, it may be desirable to view different plays or portions of the event from different points of view to improve the visualization of team formation and the like. It further may allow the viewed experience the point of view of the athlete participating in the event, competition. A viewer may therefore be able to experience the viewpoint of a football quarterback throwing a touchdown pass in the Superbowl, a soccer forward scoring a goal in the World Cup, or a baseball batter hitting a home run in the World Series, among other athletes and events.

When the display engine 204 reconstructs the event, competition, or game from data recorded and/or streamed in substantially real time from the data recording system 202, it may reproduce the athletes as avatars. An avatar may be a virtual representation of appearance of the athlete themselves or may be any other suitable avatar. For example, a viewer may be entertained by replacing the avatar of a star soccer or football player with an avatar that resembles or reflects his or herself. On the other hand, a coach may desire a more simple avatar when analyzing team formations and the like. For example, a football coach may utilize "X" and "O" avatars to represent offense and defense in a football game.

Figure 10:
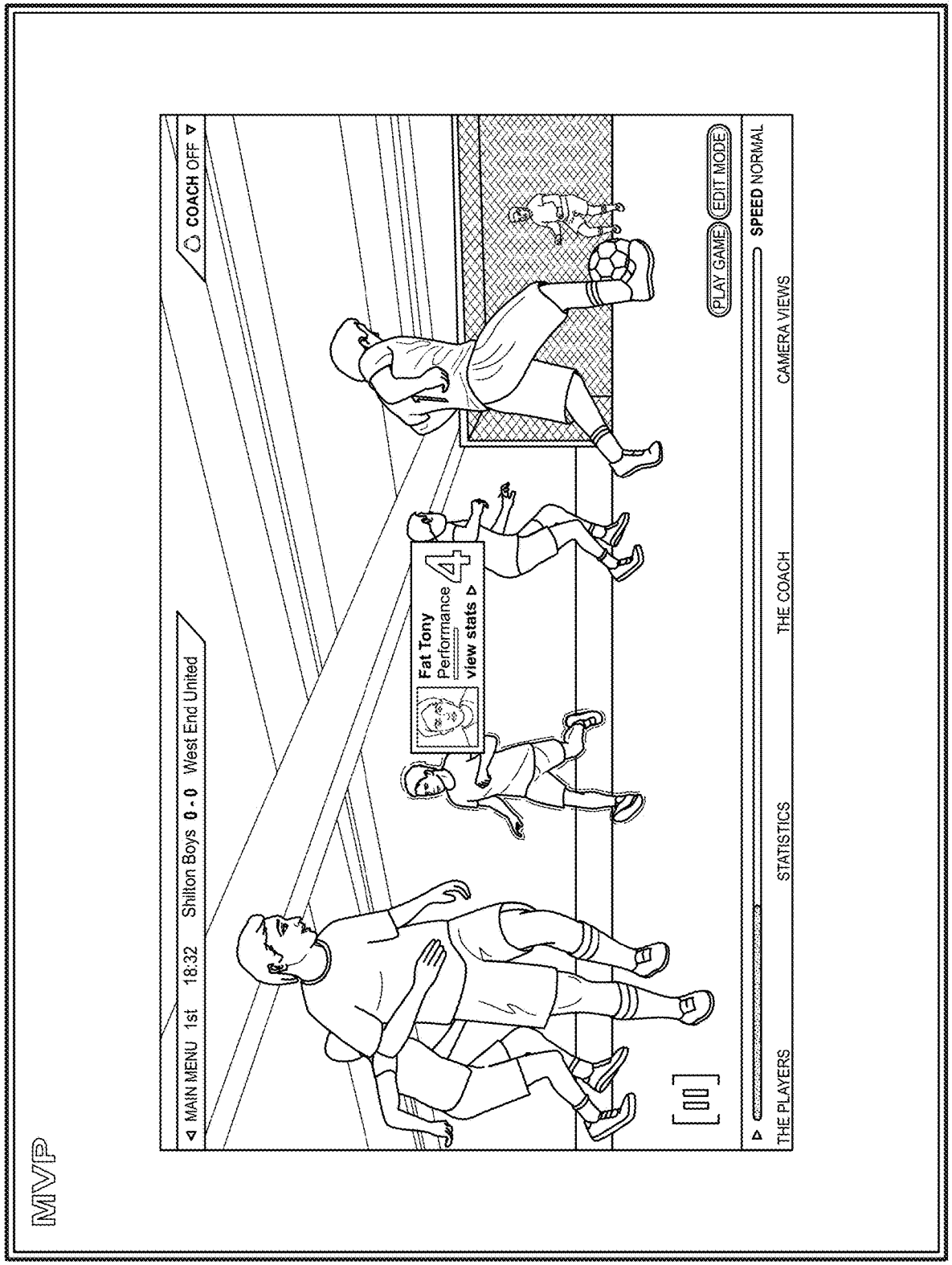
FIGS. 10 and 11 illustrate additional information interfaces according to one or more aspects of the invention described herein.
Figure 11:
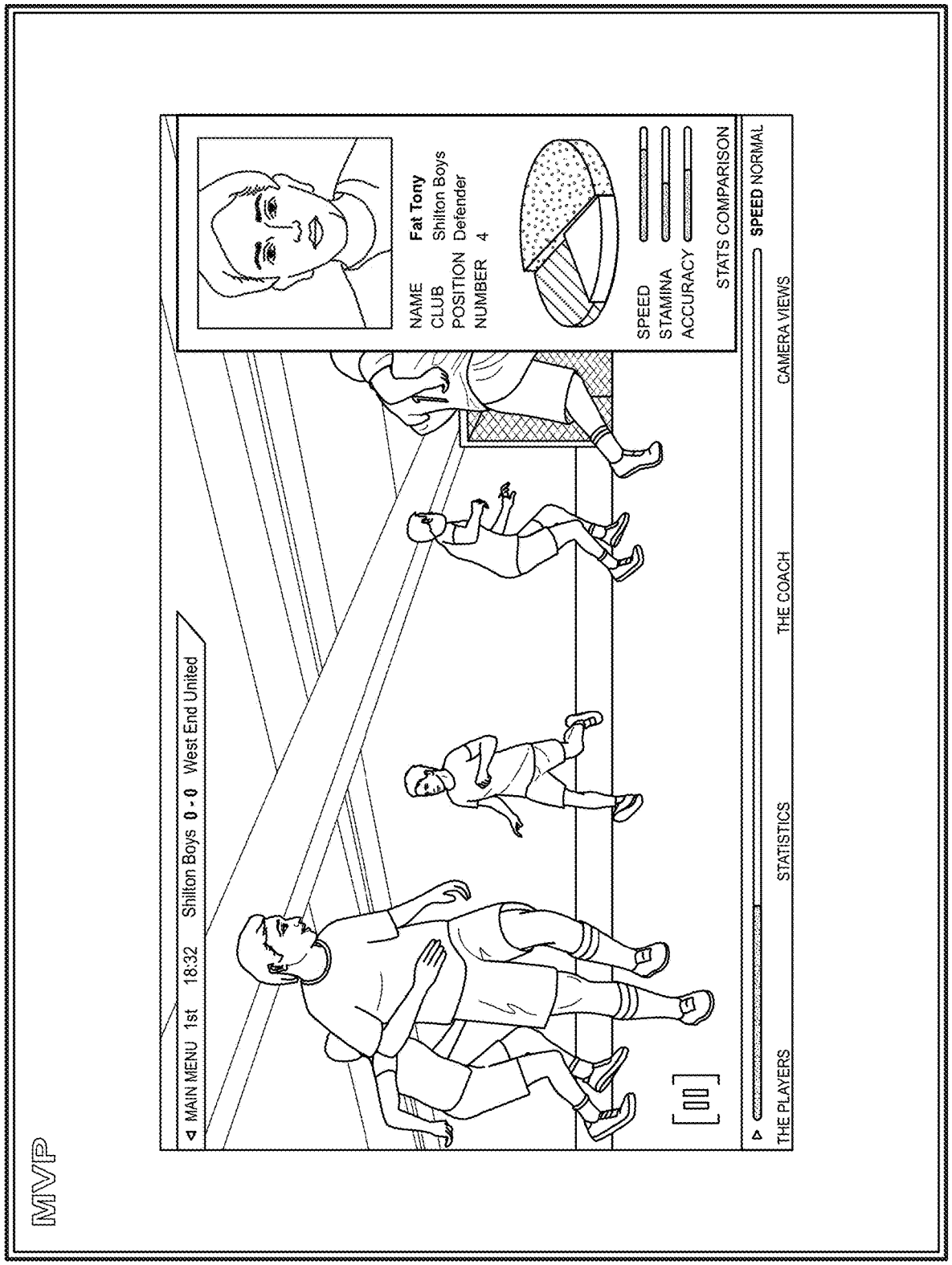

During the viewing or replay of an event, competition, or game, a viewer may select an individual athlete or team to review their athletic performance metrics as introduced above. For example, as illustrated by FIG. 10, upon selection of an individual (e.g., by mouseover or the like), the display engine 204 may display the name of the athlete, their number or other identifier, and one or more summary statistics pertaining to the athletic performance of the athlete. Further, as illustrated by FIG. 11, the viewer may choose to view more detailed athletic performance statistics and/or details related to the athlete's team and position. For example, the athletic performance metrics may represent current or real time athletic performance (e.g., current speed) or may reflect accumulated or average athletic performance (e.g., total distance run, average speed, and the like). The display engine 204 may also generate a heat map to illustrate the frequency with which an athlete occupies a particular portion of the arena, pitch, or field area. Such a heat map may resemble a color-coded, two-dimensional topographical map of the athlete's position. Areas the athlete frequently occupies may appear, for example, red while areas the athlete infrequently occupies may appear, for example, blue.

Figure 13:
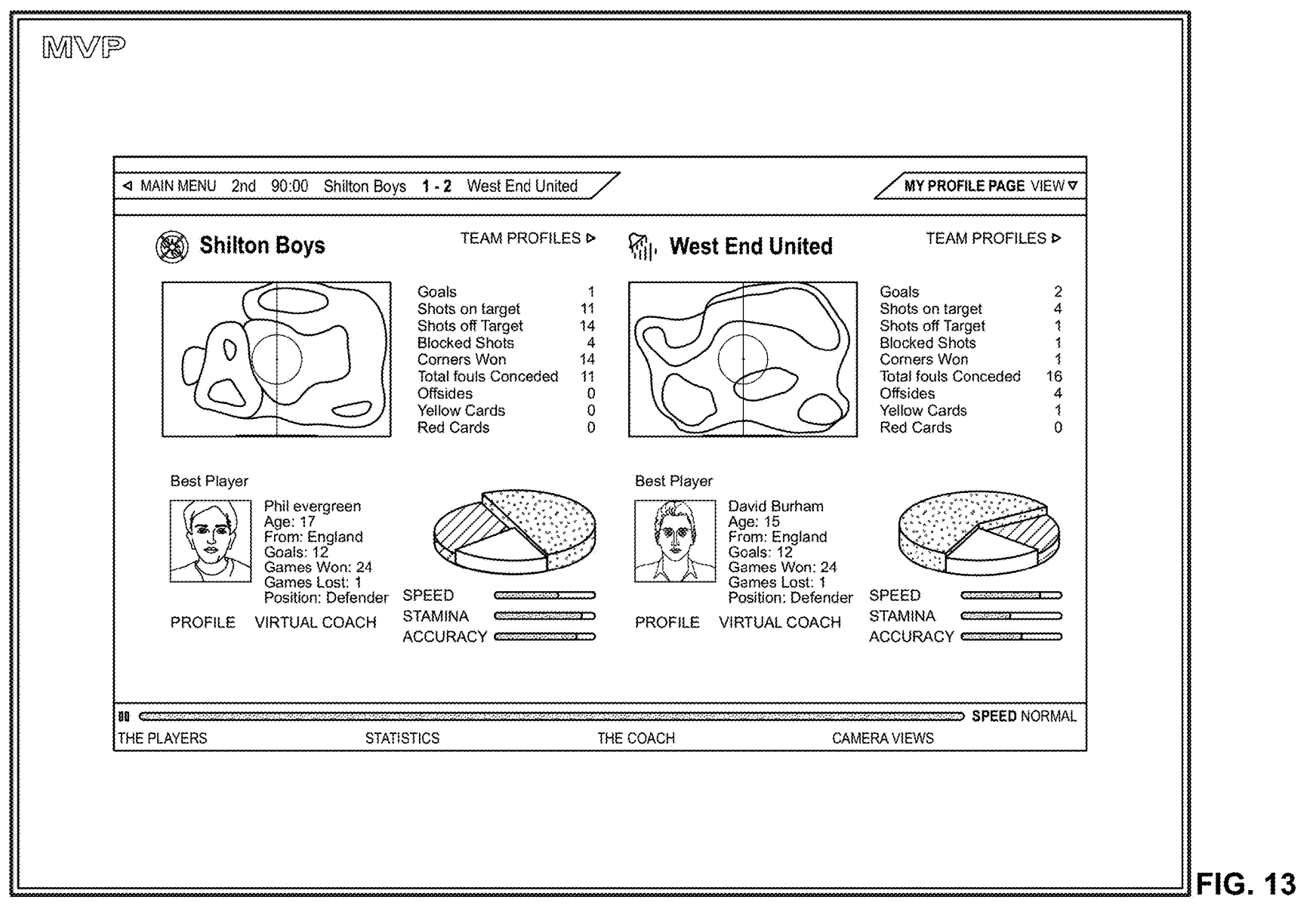

FIG. 13 illustrates additional details for the event, competition, or game. For example, the display engine 204 may display a comparison between two teams and/or one or more individual athletes. More specifically, the display engine 204 may display a cumulative heat map for each team. Additionally, the display engine 204 may display statistics related to each team. For example, for an American soccer/European football game between two teams, the display engine 204 may display goals, shots on target, shots of target, blocked shots, corners won, total fouls conceded, offsides, yellow cards and red cards. The display engine 204 may display alternate and/or additional details depending on the nature of the event, competition, or game.

FIG. 13 illustrates that the display engine 204 may further indicate details related to the best player on each team. In doing so, the display engine 204 may display the avatar for each player, and details associated with each player. For example, if the players are American soccer/European football players, the display engine 204 may display each player's name, age, country of origin (and/or team origin), number of goals scored, number of games won, number of games lost, and/or position played. Display engine 204 may display alternate and/or additional information depending on the nature of the event, competition, or game.

FIG. 13 illustrates that display engine 204 may further display a graphical representation of one or more performance metrics. The performance metrics may be cumulative performance metrics for the team or they may be individual performance metrics for one or more individual players (in an embodiment, the best player for each team). The performance metrics may include metrics related to speed (e.g., based on their top speed and/or average speed), their stamina (e.g., based on maintaining their speed throughout the event, competition, or game), and/or their accuracy/technique (e.g., passing accuracy, hitting accuracy, shot accuracy, and the like). FIG. 13 further shows that data can be represented in the form of pie charts and it is further understood that data can be displayed in other graphical forms.

Figure 25:
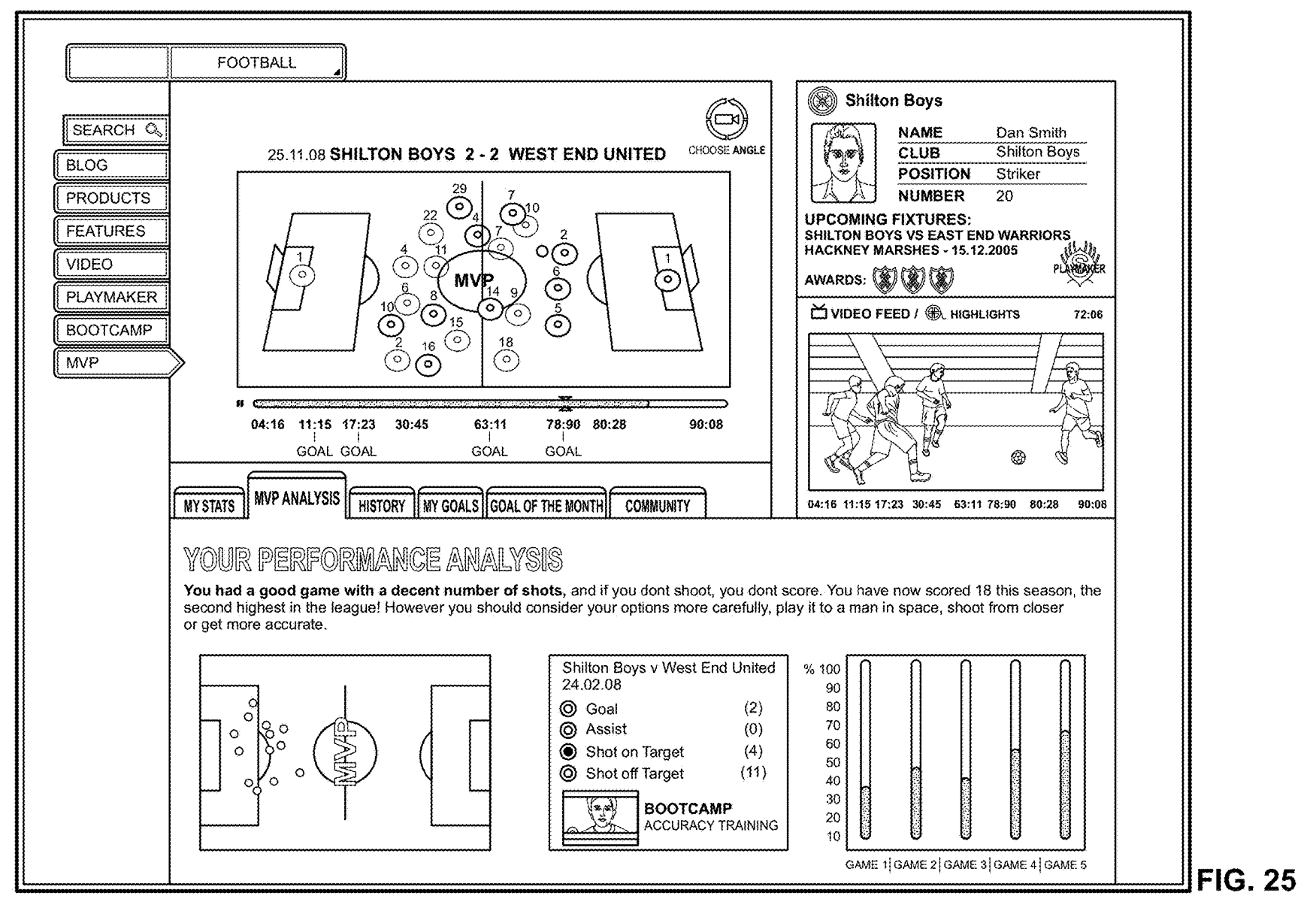
Figure 26:
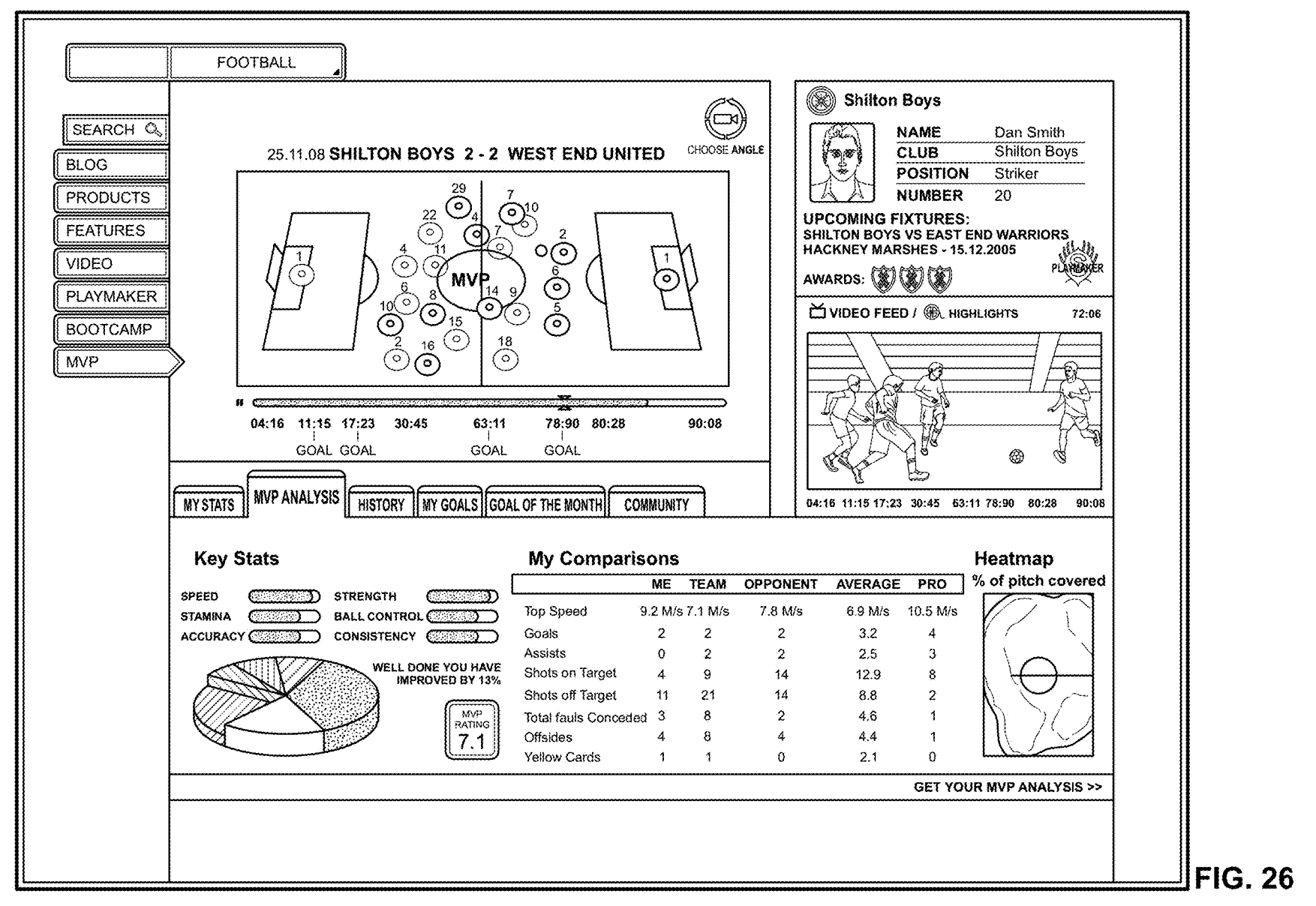

FIGS. 25 and 26 illustrate an alternate graphical representation of an event, competition, or game including one or more performance metrics associated therewith. More specifically, FIGS. 25 and 26 illustrates that the display engine 204 and display 206 of an embodiment may display a virtual representation of one or more athletes in the sports arena, pitch, or field 210. For example, each player on a team may be displayed with a marker or the like within the virtual representation of the sports arena, pitch, or field 210. Each player may be further displayed with their jersey number. Additionally, members of separate teams may be identified by the color and/or symbol of their marker. The virtual representation of the event, competition, or game within the sports arena, pitch, or field 210 may be a static representation or a dynamic representation. For example, the display engine 204 may display a video of the virtual event, competition, or game. The viewer may play and/or pause the video to produce a snapshot of the game action (e.g., player locations) at a given time during the event, competition, or game. Further, the display engine 204 may provide a timeline for the event, competition, or game with important events identified on the timeline (e.g., a scoring event or the like). For example, the event, competition, or game timeline may indicate specific times at which a goal is scored so that a viewer may jump along the timeline to view the event, competition, or game at that time.

FIGS. 25 and 26 further illustrate that the display 206, in conjunction with data engine 204, may provide statistical and/or analytical feedback of an individual athlete's and/or team's performance. For example, the display engine 204 and display 206 may display athletic performance statistics, an athletic performance analysis, an athletic performance history, scoring details (e.g., goals or points scored, a relative ranking or goals or points scored, and the like), and a link to a community in which data, information, comments, personal messages, audio visual content and the like may be shared.

FIG. 25 more specifically illustrates that the analysis may include, among other features, an indication of location within the arena, pitch, or field from which an individual athlete or team member made a scoring attempt (e.g., shot on goal, pass, kick, and the like depending on sport). Successful scoring attempts may be represented by a marker with an alternate color and/or pattern. The display engine 204 may also display a narrative assessment and/or summary of the individual athlete's and/or team's athletic performance. Based on the individual athlete's and/or team's athletic performance, the display engine may suggest one or more training programs. For example, and as illustrated by FIG. 25, an individual athlete may attempt many shots on goal, but may only rarely or sporadically score. In such a situation, the display engine of an embodiment may recommend one or more training programs designed to increase shot accuracy. Further, the display engine 204 may display a graphical representation of the athletic performance for which it recommended training. Such a graphical representation may include a historical view and/or analysis so that the individual athlete may track their progress. For example, should the individual athlete undertake an accuracy training program, the display engine may provide a graphical display (e.g., a bar chart displaying the percentage of shots on goal that were successful) of their accuracy over the course of several games. Other athletic performance graphical representations are possible depending on the sport and/or training program.

FIG. 26 illustrates additional statistics and/or analysis as provided by the display engine 204 of an embodiment. For example, the display engine 204 and display 206 may provide one or more bar charts indicating an individual athlete's and/or team's statistics such as speed, stamina, accuracy, strength, ball control, consistency, and the like (depending on the sporting event, competition, or game in which the individual athlete and/or team participates). The individual athlete's and/or team's athletic performance may be displayed in a numerical value or as a percentage of a maximum value. Further, the individual athlete's and/or team's cumulative athletic performance may be displayed as a single numerical and/or symbolic metric. The cumulative athletic performance indication may depend on one or more of the individual athlete's and/or team's statistics such as speed, stamina, accuracy, strength, ball control, consistency, and the like (depending on the sporting event, competition, or game in which the individual athlete and/or team participates).

FIG. 26 further illustrates that the display engine 204 of an embodiment may provide a comparison between individual athletes, teams, opponents, and the like. For example, the display engine 204 may list one or more athletic performance metrics for an individual athlete such as top speed, goals scored, assists, shots on target, shots of target, total faults conceded, offsides, and yellow cards. The display engine 204 may display alternate and/or additional performance metrics depending on the sporting event, competition, or game in which the individual athlete participates. For each performance metric, the display engine 204 may further display the team average, an opponent's average, a league and/or overall average, and an indication of a professional level. Accordingly, an individual athlete may not only compare their performance with their team average and/or opponent average, but they may also have an indication of how their athletic performance compares to that of a professional athlete.

Figure 14:
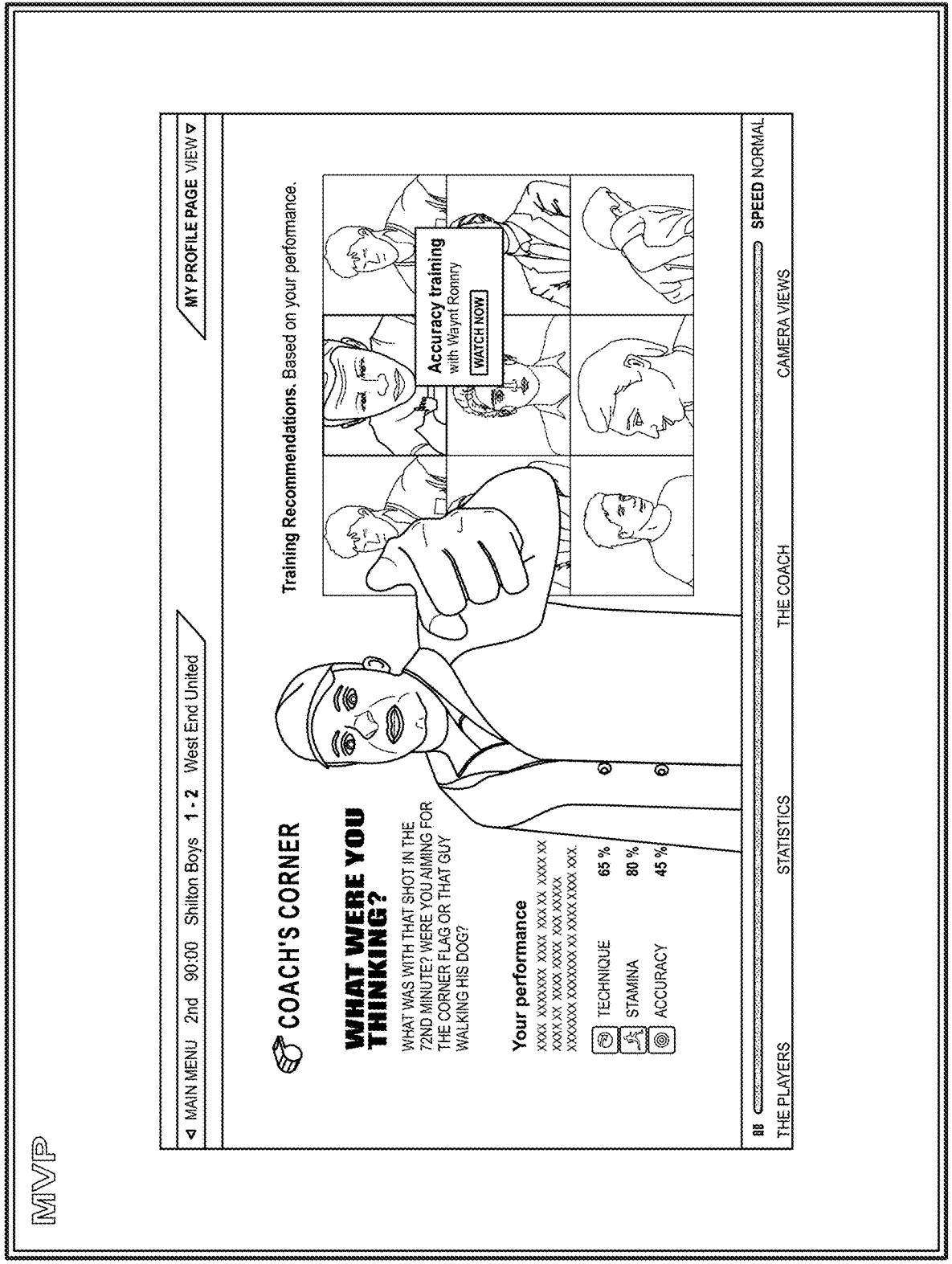
FIG. 14 illustrates another coaching interface according to one or more aspects of the invention described herein.

FIG. 14 illustrates that the display engine 204, based on the data collected by the data recording system 202 and analyzed by the data engine 204, may provide a virtual coach and/or training tool. For example, the display engine 204 may indicate, based on generated performance metrics, that an individual athlete's and/or team's speed, stamina, and/or accuracy/technique may need improvement. The display engine 204 may further provide a narrative description of the individual athlete's and/or team's performance and why (e.g., based on a comparison to threshold performance and/or other individual athletes or teams) improvement is necessary.

Figure 12:
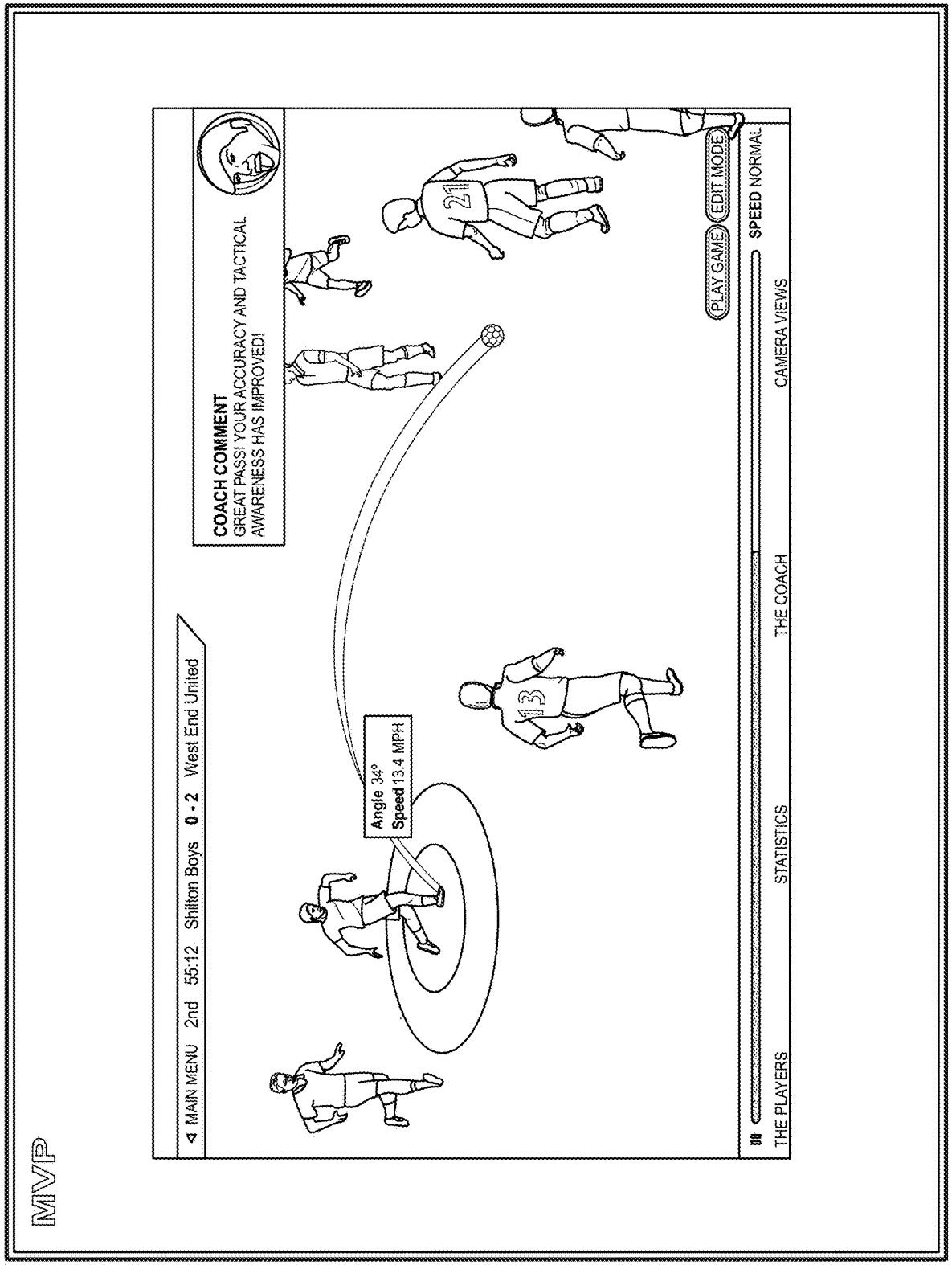
FIG. 12 illustrates a coaching information interface according to one or more aspects of the invention described herein.

More specifically, based on the data accumulated from the event, competition, or game, the display engine 204 may provide coaching tools in response to an analysis of the game as illustrated by FIG. 12. For example, the data engine 204 may reveal that the average or maximum speed of a particular athlete or team of athletes decreases toward the end of the game. In response display engine 204 may indicate to the coach or viewer that the particular athlete or team of athletes may consider additional conditioning or endurance training. The data engine 204 may further reveal that soccer or football passes to and/or from particular athletes are less successful than between other combinations of players. The display engine 204 in this example may suggest accuracy training or the like. Myriad of such examples exist depending on the nature of the sport captured by the data recording system 202, analyzed by the data engine 204, and presented by the display 206.

The display engine 204 may further offer instructional commentary, videos, and the like based on the training it recommends. For example, if the display engine 206 recommends accuracy training to an athlete, it may further offer one or more instructional videos for the athlete to review. For a given performance improvement (e.g., speed, stamina, accuracy, technique or the like depending on the sport), there may be multiple training/coaching videos from which to choose, for example based on the experience level or magnitude of necessary improvement of the athlete and/or team. The display engine 204 may further track the athlete's performance over time (e.g., a season) to identify trends in athletic performance and/or whether the training is improving the athlete's performance.

Figure 15:
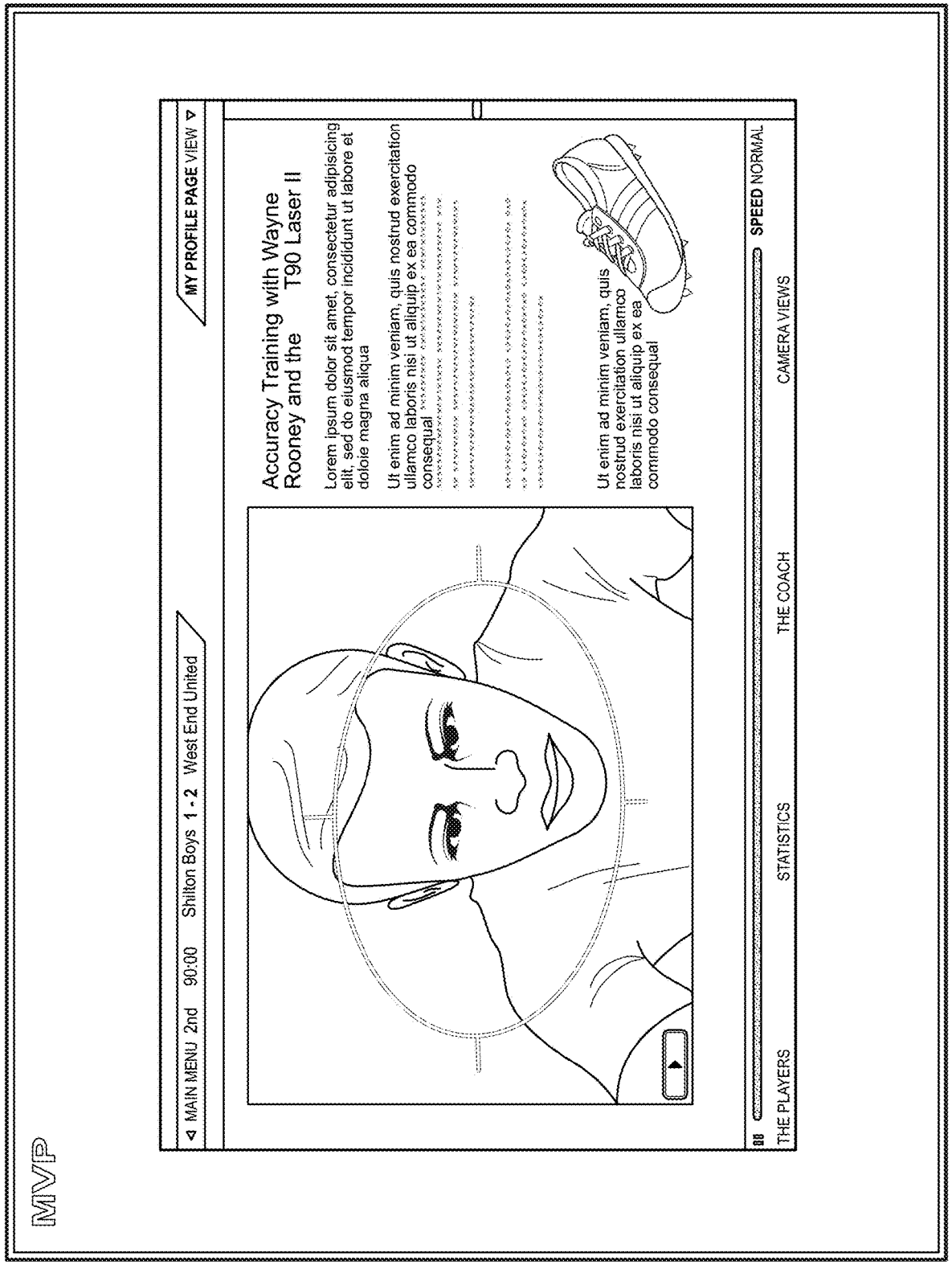
FIG. 15 illustrates a training interface according to one or more aspects of the invention described herein.
Figure 17:
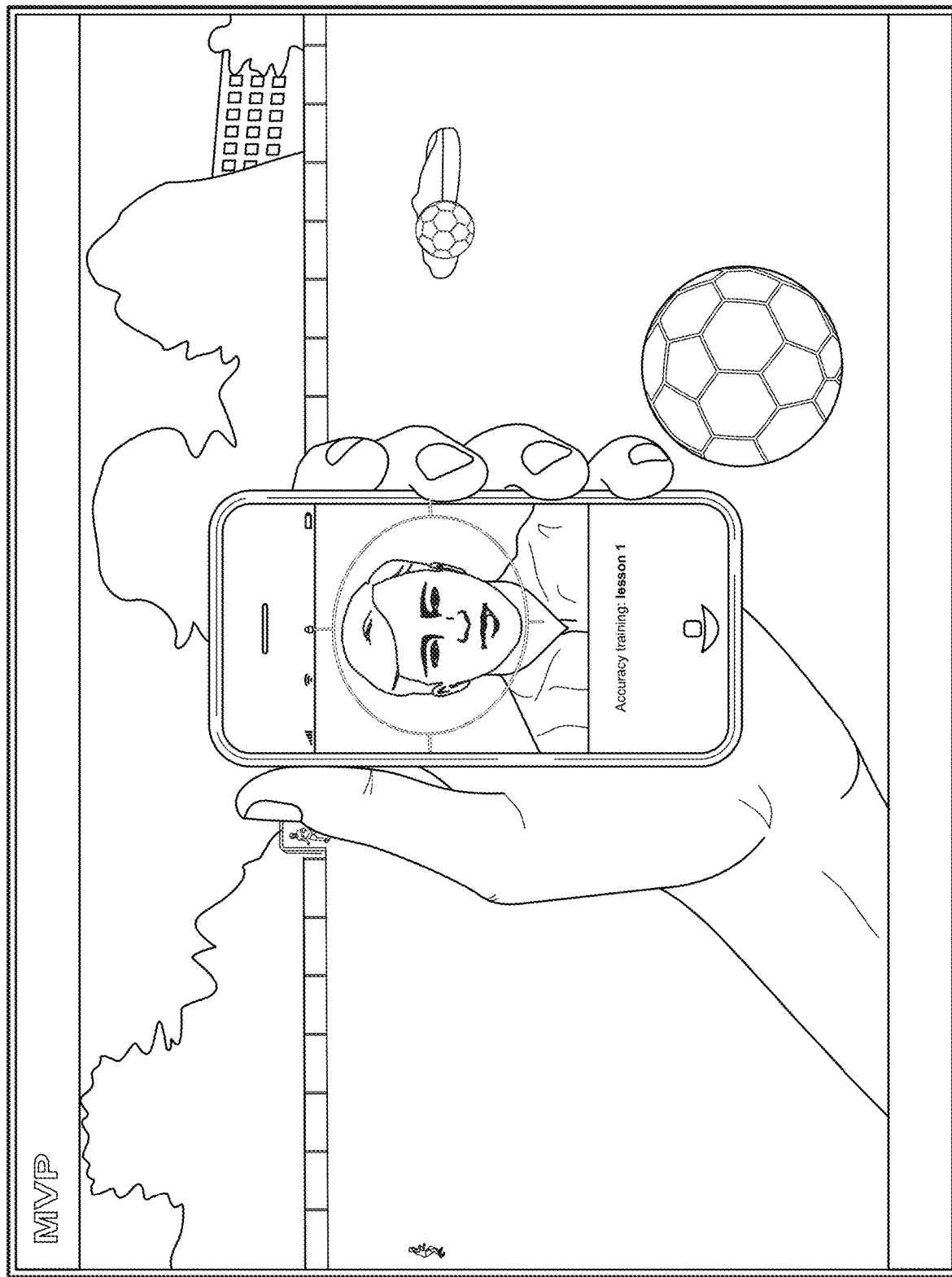
FIG. 17 illustrates an additional information interface according to one or more aspects of the invention described herein.

FIG. 15 illustrates the display engine 204 providing an exemplary training/coaching video to improve an athlete's and/or team's accuracy. The display engine 204 of an embodiment may provide additional narrative information to supplement the video in the form of text. Further, the video and/or narrative may provide equipment suggestions. For example, if the data engine 204 determines that the athlete is slipping or otherwise losing traction (e.g., while running, kicking, and the like depending on the sport) the display engine may suggest that the athlete and/or team alter their equipment, for example footwear choice and spike length, to improve their performance. FIG. 17 illustrates that in addition to a computer or the like, the display engine may provide one or more training/coaching videos on a portable device, for example an digital music player, mobile telephone, or any other portable electronic device.

Figure 16:
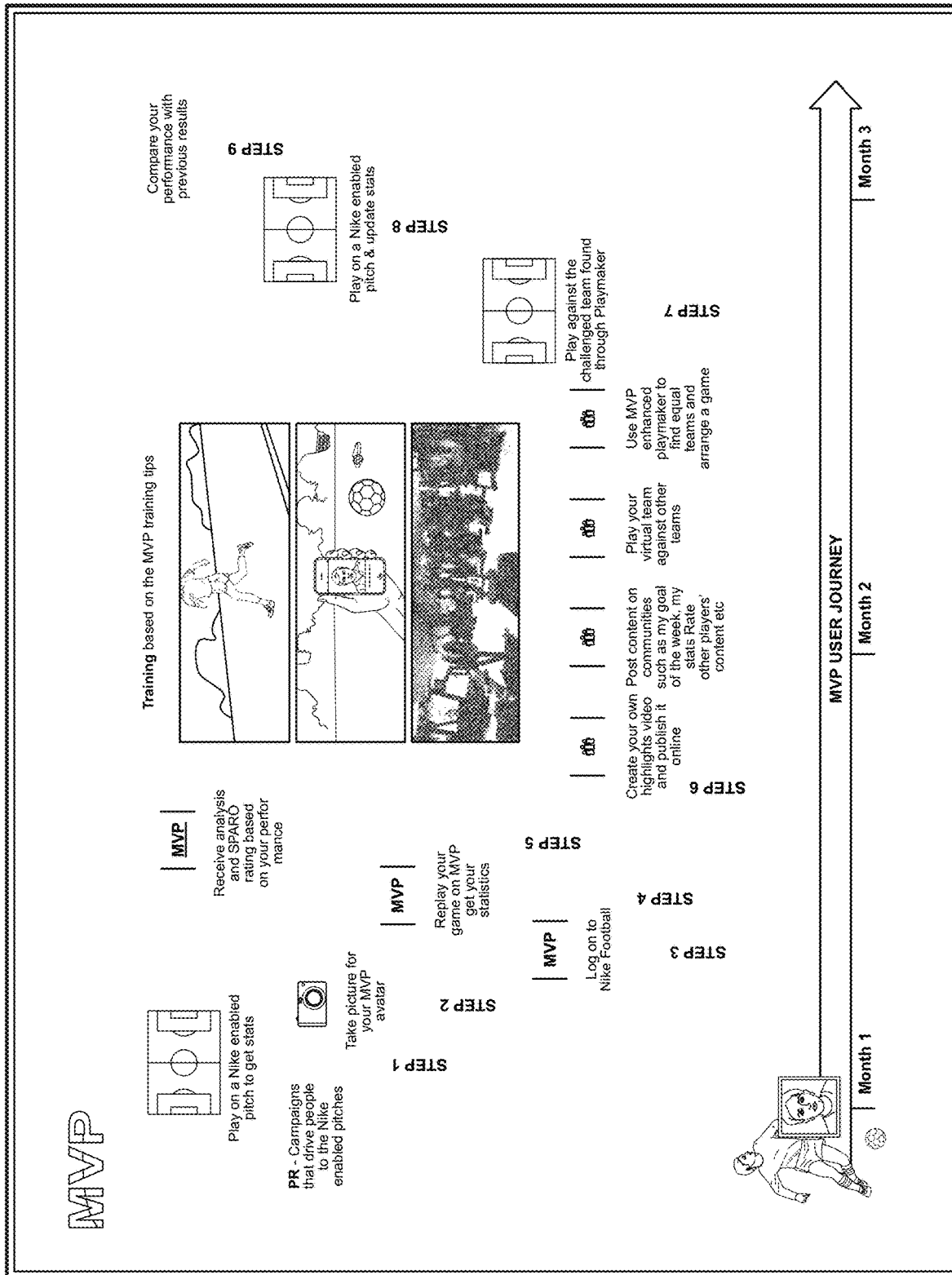
FIG. 16 is a schematic view of a user journey according to one or more aspects of the invention described herein.
Figure 24:
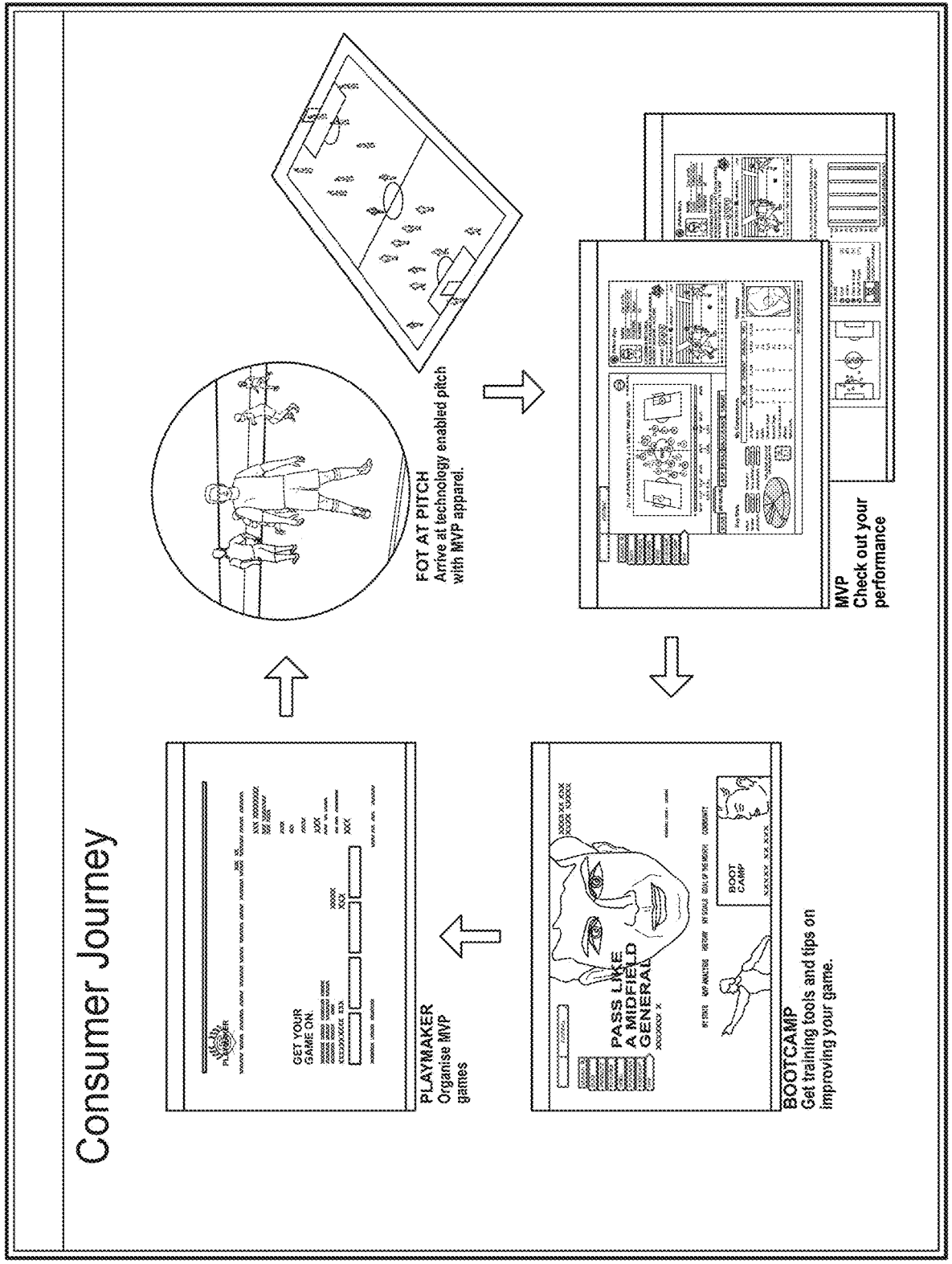
FIG. 24 is a schematic view of another user journey according to one or more aspects of the invention described herein.

FIGS. 16 and 24 illustrate exemplary user journeys. For example, a user can utilize the system and get performance statistics and training tips. A user can also utilize other matching systems to find other teams to play and utilize the system of the present invention. A user can also create a highlight video, connect content to other networking services, play one's own team against another virtual team. The system could also be used to find an actual team to play that corresponds to a virtual team in the system. FIG. 24 shows additional features of the system and display engine 204 such as providing the ability of the user to link to organizing games with other teams, obtaining training information and reviewing previous performances.

Figure 18:
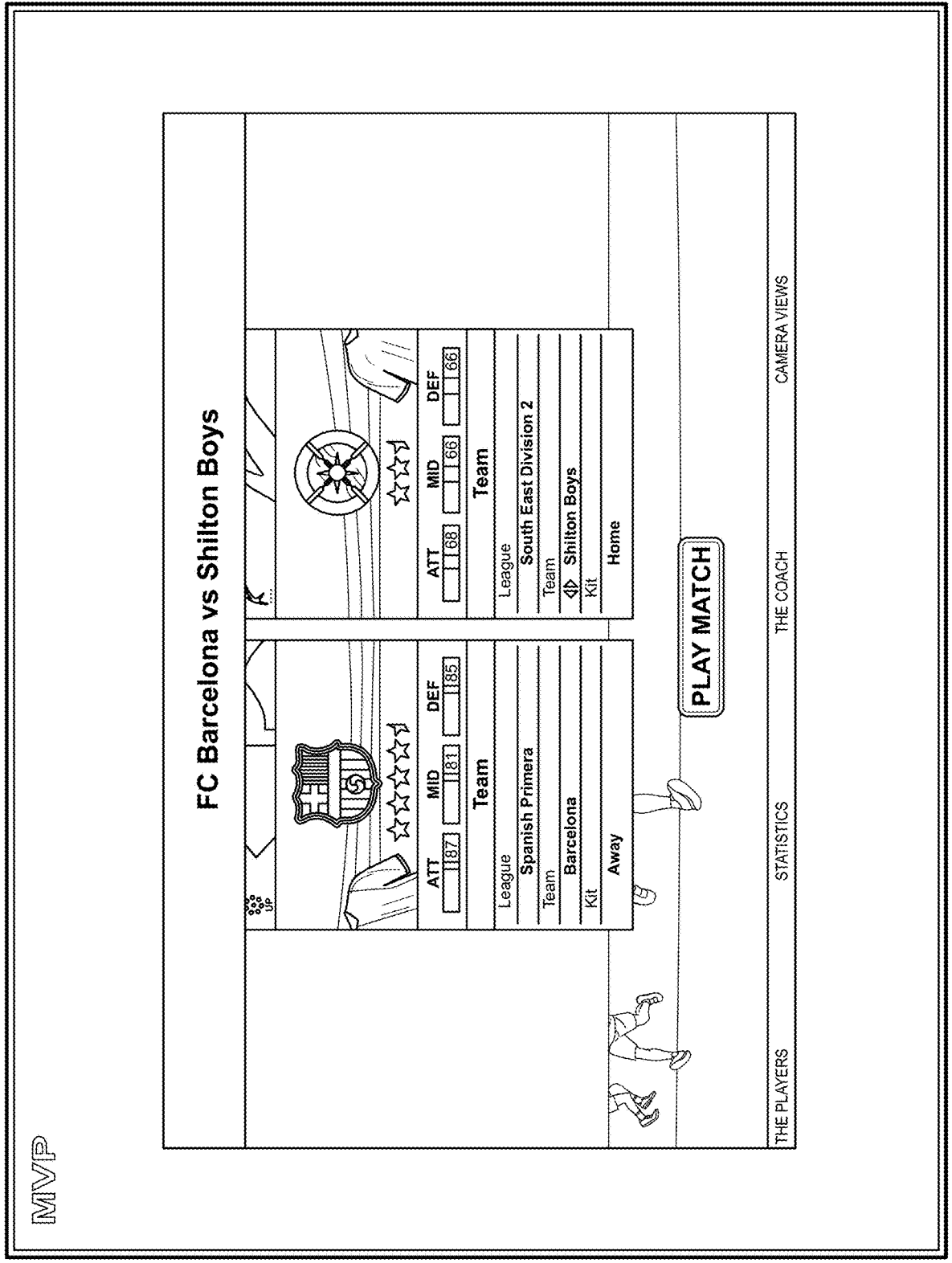
FIG. 18 illustrates another comparison interface according to one or more aspects of the invention described herein.

FIG. 18 illustrates that the data accumulated by the data engine 204 for multiple individuals athletes and/or teams may be compared to generate individual and/or team matchups. For example, two or more individuals and/or teams may be compared by one or more performance metrics (e.g., speed, stamina, accuracy, technique or the like depending on the sport) to determine whether or not they may be relatively competitive. Other performance metrics may apply. For example, a team's performance metrics may be specific to offense and/or defense. Accordingly, a team having a high performance offense and mediocre defense may match up competitively with a team having a high performance defense and a mediocre offense. Other combinations of relative strengths and weaknesses for individuals and/or team may be useful to generate competitions between well-matched individuals and/or teams.

In addition to facilitating competitions between, the data engine 204 in combination with the display 206 may facilitate virtual competitions between two or more individuals and/or teams. The virtual competition may provide a viewer with a simulation of a game between the two or more individuals and/or teams. Alternatively or additionally, the data analyzed by the data engine 204 regarding the performance of one or more individual athletes and/or teams may be provided as input for a sports video game. For example, the display engine 206 may further generate, alter, and/or enhance a sports video game. Specifically, the real world performance of one or more individual athletes and/or teams as collected by the data recording system 202 and determined by data engine 204 may contribute to the performance of the one or more individual athletes and/or teams when those individuals and/or teams are virtually playing in a sports video game. For example, if the athlete exhibits inaccurate passing in a real world game, the passing accuracy of their respective video game player will similarly exhibit inaccurate passing. To improve the athletic performance of their virtual sports video game player, the athlete may be required to improve their real world athletic performance, for example by watching coaching videos suggested by the display engine 206 in response to the display engine 204 identifying an area or areas in which an athlete's athletic performance needs improvement as introduced above.

The display engine 204 may also allow a sports video game player to experience real world events, competitions, or games as if they were playing in the event, competition, or game themselves. For example, the video game player may substitute themselves for another athlete in a real world event, competition, or game (e.g., with an avatar and with a set of athletic performance abilities in an embodiment determined by their real world abilities as discussed above). Alternately, a video game player may substitute athletes from other teams or eras into the video game based on their predetermined athletic performance abilities or those captured and calculated by the data recording system 202 and data engine 204 of an embodiment.

Figure 19:
FIG. 19 illustrates another information interface allowing player comments and other applications according to one or more aspects of the invention described herein.

As illustrated by FIG. 19, athletes can also add commentary to the game or construct a post-game interview based on the game. For example, the display engine 204 may generate a virtual interview during which one or more players are represented by their avatars. In an embodiment, the virtual interview may include audio and visual (e.g., video) information. Alternately or additionally, the display engine 204 may present virtual interviews in text or narrative form. In an embodiment, the display engine 204 may accept and display comments from other athletes, teams, or viewers. Additionally, the display engine 204 may link to one or more videos representing, for example, plays by the athlete being currently virtually interviewed. The display engine 204 may also provide links to related videos, such as those representing the interviewed athlete's plays in other events, competitions, or games. The related videos may alternately or additionally include videos of other athlete's in the same event, competition, or game. Further still, the display engine 204 may present links to promotional videos that may, in an embodiment, promote additional events, competitions, or games and/or athletic equipment.

Figure 20:
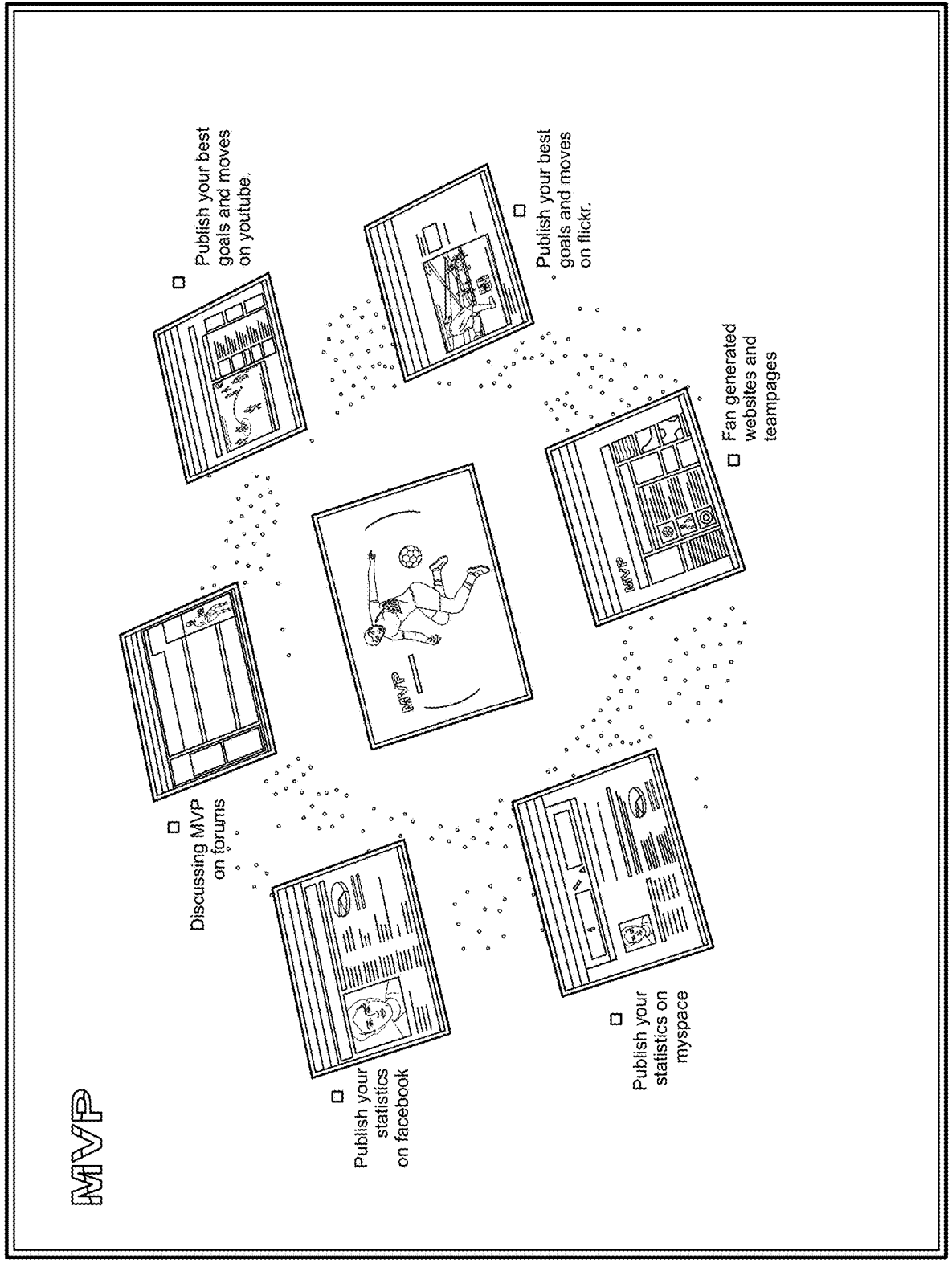
FIG. 20 is a schematic view showing additional communication capabilities of the system according to one or more aspects of the invention described herein.

As noted above, an athlete can replay and review an event, competition, or game and the performance metrics and/or statistics associated therewith with the display engine 204. The data engine 204 and/or display 206 may also communicate with other systems such as social networking websites or team-oriented websites. For example, FIG. 20 illustrates exemplary systems with which the data engine and/or display engine 204 may communicate. More specifically, the data engine 204 and/or display 206 may communicate data, statistics, performance metrics, audio content, video content, and the like with a forum website, a video website, a photo website, a fan-generated website, a team-oriented website, a social network service, and/or a sports network service. The embodiments are not limited in this context.

Figure 21:
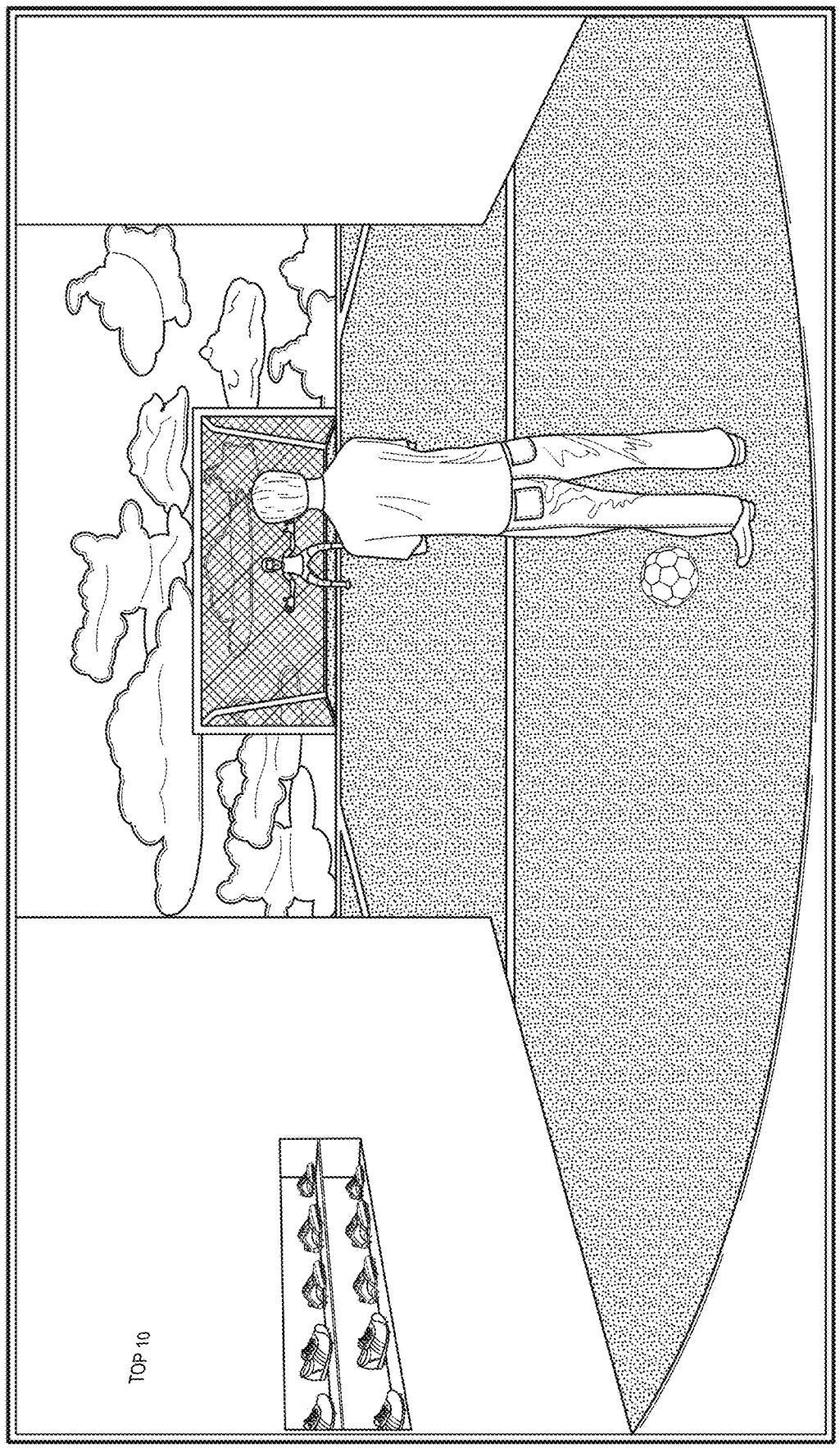
FIGS. 21-22 show additional applications of the system of the present invention in a retail setting.
Figure 22:
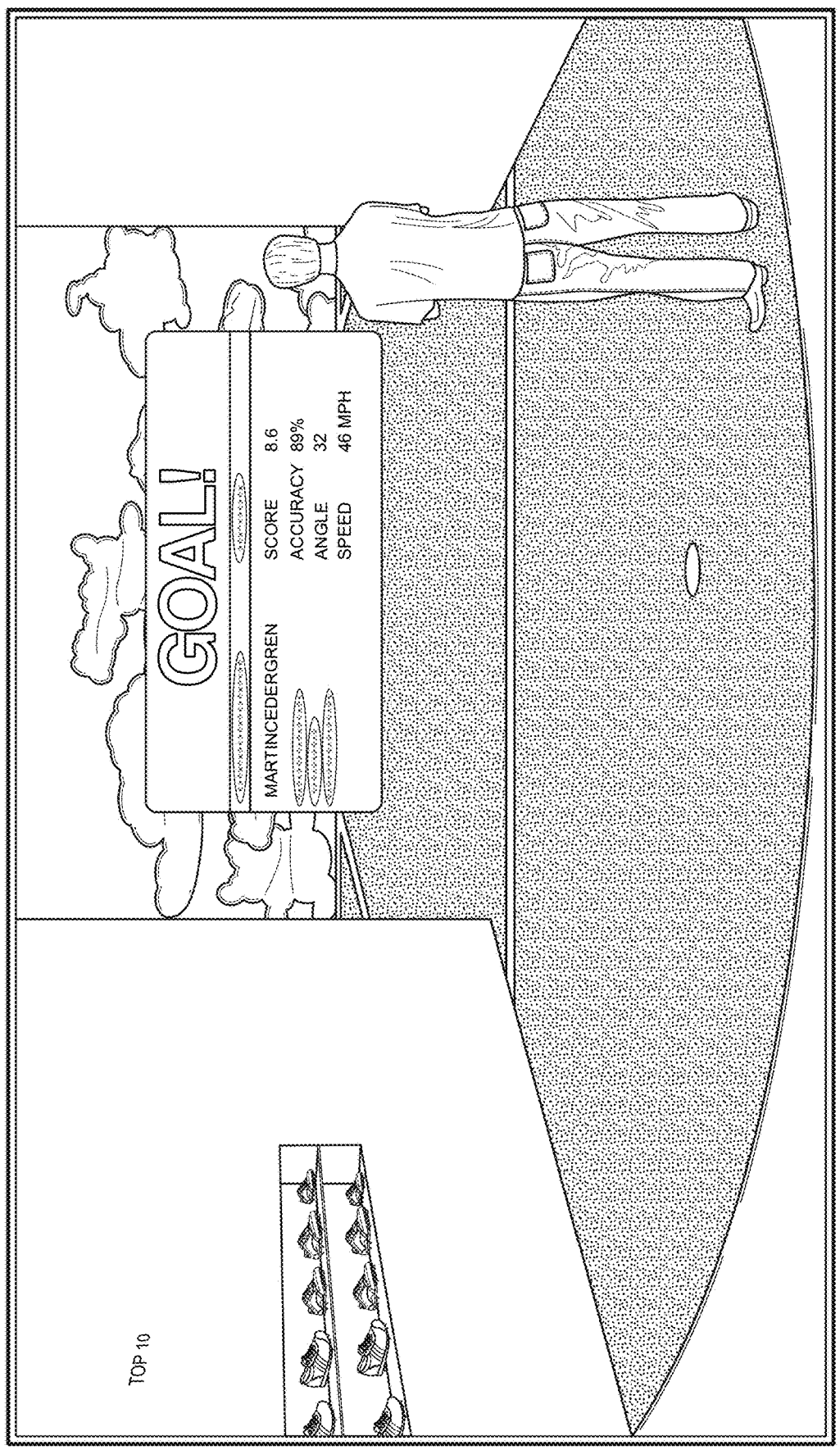

It is further understood that the system 200 could be set up in a retail or commercial location wherein customers could be filmed performing a sports activity in an abbreviated fashion wherein the display engine 206 can display the customer in a unique matter performing the activity just filmed. For example, FIG. 21 illustrates a customer at a retail location that may be recorded performing an athletic activity by the data recording system 202. In conjunction with the data engine 204, the display 206 may insert a representation of the customer (e.g., an avatar or the like) into a virtual event, competition, or game setting. For example, as illustrated by FIG. 21, the data recording system 202 may record the customer shooting at an American soccer/European football goal. Myriad other virtual events, competitions, or game settings may displayed by the display engine. Based on the analysis by the data engine 204, the display 206 may thereafter indicate if the customer scored a goal such as shown in FIG. 22. In addition, the display 206 may provide an indication of the customer's athletic performance. For example, in addition to indicating whether or not the customer scored a goal, the display engine may further indicate the accuracy of the shot, the angle of the shot, the speed of the shot, and an overall assessment and/or score of the shot. The display 206 may present additional and/or alternate indications depending on the sport and/or virtual event, competition, or game setting.

Figure 23:
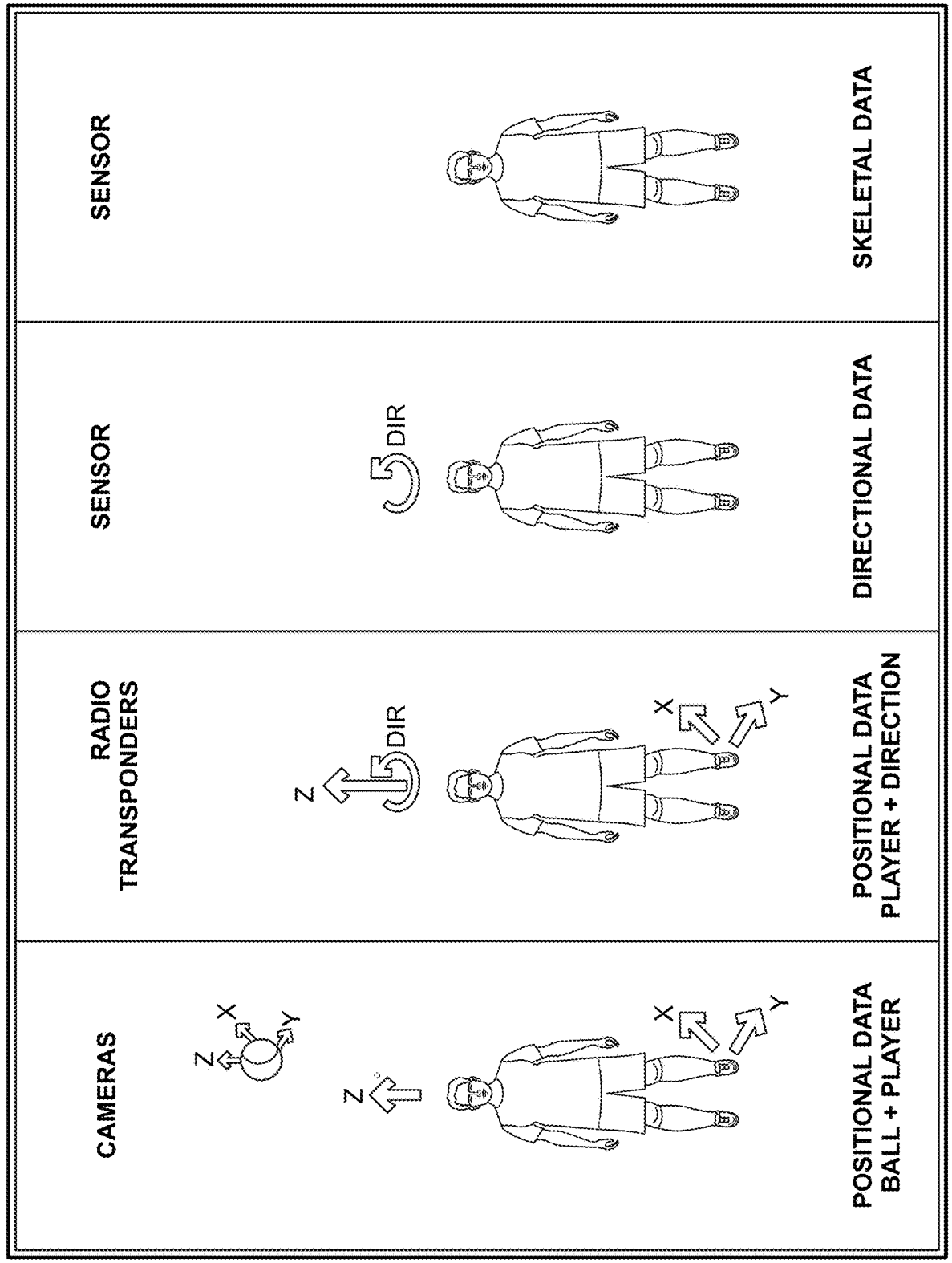
FIG. 23 is a schematic view showing various data gathering applications according to one or more aspects of the present invention.

FIG. 23 illustrates that the data recording system 202 may collect positional and/or athletic performance data from one or more sources. As noted above a sports arena, pitch, or field 210 area may be covered by multiple computer-controlled cameras (e.g., camera assemblies 212 and 214) that interoperate and utilize stereoscopy or similar measurement techniques to capture, process, and deliver the three-dimensional coordinates (e.g., (x,y,z)), speed, and acceleration of each moving object in the sports arena, pitch, or field 210 in the form of a data feed to the data engine 204. The moving objects include individual athletes including referees or officials participating in an event, competition, or game located within the arena, pitch, or field 210, as well as the ball, puck, or similar athletic implement specific to the event, competition, or game.

The data recording system 202 may collect alternate/additional data than that collected by one or more cameras (e.g., camera assemblies 212 and 214). For example, each individual athlete may be equipped with one or more sensors and/or radio transponders. More specifically, one or more radio receivers positioned adjacent to and/or within the sports arena, pitch, or field 210 may receive positional information from radio transponders coupled to one or more individual athletes and/or athletic implements. For example, the radio transponder may be coupled to a Global Positioning System (GPS) receiver to transmit the positional information. Alternately, the position of a radio transponder may be calculated by the one or more radio receivers (e.g., based on the time difference among the receipt of the radio transponder by multiple radio receivers or similar method). Additional sensors (e.g., accelerometers, heart rate monitors, blood oxygen saturation monitors, and the like may provide alternate and/or additional data related to the position, movement and/or biometrics of individual athletes that may be transmitted in substantially real time or recorded for later correlation with other positional and/or athletic performance data. Sensors may be mounted in an athlete's shoes, apparel or otherwise be mounted on the person. The ball or puck may also include a sensor as well as other portions of the pitch or field.

The present invention provides several benefits. Because of its simplicity, the system allows even amateur teams and athletes the ability to obtain valuable performance related data. Consequently, athletes become more inspired and motivated to participate in more games and events thus increasing skills and overall fitness levels. In addition, the ability to watch a "replay" of a game just played in a unique form such as in animation and with the use of avatars is further enjoyable for athletes. Athletes can also receive valuable training advice based more on more accurate performance data associated with the athlete. The training advice is, therefore, more focused and more likely to result in a positive impact on the athlete.

Aspects of the invention have been described in terms of illustrative embodiments thereof. Numerous other embodiments, modifications, and variations are within the scope and spirit of the appended claims. For example, the steps illustrated in the figures may be performed in other than the recited order, and that one or more steps illustrated may be optional in accordance with aspects of the disclosure. Of course, the methods and systems of the above-referenced embodiments may also include other additional elements, steps, computer-executable instructions, or computer-readable data structures. In this regard, other embodiments are disclosed herein that can be partially or wholly implemented on a computer-readable medium, for example, by storing computer-executable instructions or modules, or by utilizing computer-readable data structures.

I claim:
1. A method comprising:
receiving athletic performance data associated with a first individual;
generating a video game of an athletic event in an animated form, wherein the first individual is represented by an avatar and a performance of the avatar in the video game is based on the received athletic performance data associated with the first individual;
generating a recommendation for improving one or more athlete performance metrics of the first individual based on the received athletic performance data;
displaying a video game interface including the generated video game in a video game panel and the recommendation for improving one or more athlete performance metrics of the first individual in a recommendation panel;
generating a video image of the first individual in a user-selectable manner such that the video image of the first individual is user-selectable within the video game; and
responsive to receiving a user selection of the first individual in the video image, displaying one or more performance metrics from which the recommendation is based in a portion of the recommendation panel separate from the recommendation.

2. The method of claim 1, wherein the received athletic performance data includes athletic performance data from a plurality of athletic events performed by the first individual.

3. The method of claim 1, wherein a movement of the avatar during the video game is based on the received athletic performance data associated with the first individual.

4. The method of claim 1, further comprising:
displaying a prompt within the recommendation panel, wherein the prompt includes a coaching media associated with the recommendation for improving one or more athlete performance metrics of the first individual.

5. The method of claim 4, further comprising:
receiving an indication that the first individual has accessed the coaching media of the prompt in the recommendation panel; and
adjusting a virtual performance metric of the avatar based on receiving the indication.

6. The method of claim 5, wherein receiving an indication that the first individual has accessed the coaching media includes receiving athletic performance data associated with the first individual performing a coaching exercise of the coaching media.

7. The method of claim 5, further comprising:
generating an altered video game of the athletic event, wherein the performance of the avatar in the video game is altered based on the adjusted virtual performance metric.

8. The method of claim 4, wherein the coaching media includes a file from a virtual coach comprising textual, graphical, video, audio, or audiovisual output.

9. The method of claim 1, wherein the recommendation further includes an equipment recommendation.

10. The method of claim 1, further comprising:
receiving athletic performance data associated with a second individual,
wherein generating the video game of the athletic event includes a competition between a first team comprising at least the first individual and a second team comprising at least the second individual, and wherein the second individual is represented by a second avatar and a performance of the second avatar in the video game is based on the received athletic performance data associated with the second individual.

11. The method of claim 10, further comprising receiving athletic performance data from a plurality of individuals of the first team and a plurality of individuals of the second team.

12. The method of claim 1, further comprising receiving additional athletic performance data associated with the first individual, and wherein generating the video game of the athletic event include altering a performance characteristic of the first individual based on the received additional athletic performance data.

13. An apparatus comprising:
a processor; and
memory storing computer readable instructions that, when executed, cause the apparatus to:
receive first athletic performance data associated with a first individual;
receive second athletic performance data associated with a second individual;
generate a video game of an athletic event in an animated form, wherein the first individual is represented by a first avatar, the second individual is represented by a second avatar, and performances of the first avatar and the second avatar in the video game are based on the first athletic performance data and the second athletic performance data, respectively;
display a video game interface including the generated video game in a video game panel and a recommendation for improving one or more athlete performance metrics of the first individual in a recommendation panel;
generate a video image of the first individual in a user-selectable manner such that the video image of the first individual is user-selectable within the video game; and
responsive to receiving a user selection of the first individual in the video image, displaying one or more performance metrics from which the recommendation is based.

14. The apparatus of claim 13, wherein receiving first athletic performance data associated with the first individual includes determining one or more athletic performance metric based on recorded video of the first individual during an athletic event.

15. The apparatus of claim 14, wherein receiving first athletic performance data associated with the first individual includes determining one or more athletic performance metric based on sensor data from one or more motion sensors attached to the first individual during an athletic event.

16. The apparatus of claim 13, wherein the computer readable instructions, when executed, further cause the apparatus to:
generate the recommendation for improving the athlete performance metrics of the first individual based on receiving first athletic performance data associated with the first individual.

17. The apparatus of claim 16, wherein generating the recommendation includes identifying an athletic performance area for improvement based on a comparison to at least one of: a specified threshold performance and another athlete.

18. The apparatus of claim 16, wherein the computer readable instructions, when executed, further cause the apparatus to:
display a prompt within the recommendation panel, wherein the prompt includes coaching media associated with the recommendation for improving one or more athlete performance metrics of the first individual.

19. A method comprising:
receiving athletic performance data associated with a first individual;
generating a video game of an athletic event in an animated form, wherein the first individual is represented by an avatar and a performance of the avatar in the video game is based on the received athletic performance data associated with the first individual;
displaying a video game interface including the generated video game in a video game panel;
displaying, in a subpanel of the video game panel, a prompt that includes coaching media associated with improving one or more athletic performance metrics of the first individual;
generating a video image of the first individual in a user-selectable manner such that the video image of the first individual is user-selectable within the video game; and responsive to receiving a user selection of the first individual in the video image, displaying one or more performance metrics from which the coaching media is based.

* * * * *